(12) United States Patent
Park

(10) Patent No.: US 11,357,506 B2
(45) Date of Patent: Jun. 14, 2022

(54) DEVICE AND METHOD FOR ASSISTING SELECTION OF SURGICAL STAPLE HEIGHT

(71) Applicant: Chul Hi Park, Seoul (KR)

(72) Inventor: Chul Hi Park, Seoul (KR)

( * ) Notice: Subject to any disclaimer, the term of this patent is extended or adjusted under 35 U.S.C. 154(b) by 257 days.

(21) Appl. No.: 16/852,464

(22) Filed: Apr. 18, 2020

(65) Prior Publication Data
US 2020/0237372 A1 Jul. 30, 2020

Related U.S. Application Data

(63) Continuation of application No. 15/893,638, filed on Feb. 11, 2018, now Pat. No. 10,682,139.

(51) Int. Cl.
| | | |
|---|---|---|
| *A61B 17/072* | (2006.01) | |
| *A61B 90/00* | (2016.01) | |
| *A61B 17/068* | (2006.01) | |
| *A61B 17/00* | (2006.01) | |
| *A61B 90/92* | (2016.01) | |

(52) U.S. Cl.
CPC ...... *A61B 17/07207* (2013.01); *A61B 17/068* (2013.01); *A61B 17/072* (2013.01); *A61B 90/06* (2016.02); *A61B 17/00234* (2013.01); *A61B 90/92* (2016.02); *A61B 2017/00022* (2013.01); *A61B 2017/00725* (2013.01); *A61B 2017/00734* (2013.01); *A61B 2017/00818* (2013.01); *A61B 2017/0725* (2013.01); *A61B 2017/07257* (2013.01); *A61B 2017/07271* (2013.01); *A61B 2090/064* (2016.02); *A61B 2090/065* (2016.02); *A61B 2090/0811* (2016.02)

(58) Field of Classification Search
CPC .............. A61B 17/068; A61B 17/072; A61B 17/07207; A61B 17/07292; A61B 17/0644; A61B 17/115; A61B 2017/00477; A61B 2017/00017; A61B 2017/00022; A61B 2017/00398; A61B 2017/07214; A61B 2017/07271; A61B 2090/065; A61B 2090/0811
USPC ......... 227/19, 175.1, 175.2, 176.1, 180.1, 2; 606/1, 139, 153, 213, 219
See application file for complete search history.

(56) References Cited

U.S. PATENT DOCUMENTS

| | | | | |
|---|---|---|---|---|
| 5,865,361 | A * | 2/1999 | Milliman | A61B 17/068 227/176.1 |
| 10,682,139 | B2 * | 6/2020 | Park | A61B 17/072 |
| 2006/0151568 | A1 * | 7/2006 | Weller | A61B 17/07207 227/175.1 |

(Continued)

*Primary Examiner* — Scott A Smith

(57) ABSTRACT

A compression gauge cartridge for use mounted in a cartridge bay of a cartridge jaw member of a surgical stapler instrument to compress a tissue consistently to a predetermined thickness and measure a reactionary load therefrom comprises: a cartridge body; a force gauge assembly comprising a force transducer and a compression head having a tissue compression ace, wherein the force gauge assembly is supported by the cartridge body, and wherein the compression head is configured and disposed so that the tissue compression face thereof lies substantially closer to the tissue contacting surface of the anvil jaw member than the tissue supporting surface of the cartridge body; and a spacer member extending from the tissue supporting surface of the cartridge body, wherein the force gauge assembly is positioned distally with respect to the spacer member.

11 Claims, 25 Drawing Sheets

(56) References Cited

U.S. PATENT DOCUMENTS

| | | | | |
|---|---|---|---|---|
| 2006/0273135 | A1* | 12/2006 | Beetel | A61B 17/128 |
| | | | | 227/175.1 |
| 2006/0289600 | A1* | 12/2006 | Wales | A61B 17/07207 |
| | | | | 227/175.1 |
| 2008/0078806 | A1* | 4/2008 | Omaits | A61B 17/07292 |
| | | | | 227/181.1 |
| 2008/0185419 | A1* | 8/2008 | Smith | A61B 17/07207 |
| | | | | 227/179.1 |
| 2012/0228358 | A1* | 9/2012 | Zemlok | A61B 90/90 |
| | | | | 227/176.1 |
| 2013/0256375 | A1* | 10/2013 | Shelton, IV | A61B 17/0643 |
| | | | | 227/176.1 |
| 2014/0001230 | A1* | 1/2014 | Soltz | A61B 17/072 |
| | | | | 227/175.1 |
| 2014/0246474 | A1* | 9/2014 | Hall | A61B 34/30 |
| | | | | 227/175.1 |
| 2015/0209035 | A1* | 7/2015 | Zemlok | A61B 17/07207 |
| | | | | 73/1.01 |
| 2015/0316431 | A1* | 11/2015 | Collins | A61B 90/98 |
| | | | | 227/176.1 |

* cited by examiner

DEVICE AND METHOD FOR ASSISTING SELECTION OF SURGICAL STAPLE HEIGHT

CROSS REFERENCE TO RELATED APPLICATIONS

The present application is a Continuation application which claims the benefit of and priority to U.S. patent application Ser. No. 15/893,638, filed Feb. 11, 2018, now U.S. Pat. No. 10,682,139, the entire contents of which are incorporated by reference.

TECHNICAL FIELD

The present invention relates to a medical device and method for use in surgical procedures. More particularly, the present invention relates to a surgical device and method for assisting selection of surgical staple height in a surgical stapling operation.

BACKGROUND OF THE INVENTION

The utilization of mechanical tissue fastening instruments, notably, open and endoscopic surgical staplers have been increasing steadily in recent years as a substitute for suturing in joining a tissue, joining and cutting a tissue simultaneously and performing anastomosis of tubular organs belonging to the digestive system in a number of surgical disciplines. Over the years these instruments have proven to provide significant clinical benefits of improved patient outcome in addition to procedural benefits of reduced procedure time and simplified surgical tasks when compared to laborious and time consuming suturing, and related cost savings. In certain types of surgical procedures use of surgical staplers has become the preferred method of joining a tissue including the bariatric, thoracic and colorectal surgeries.

There are several known types of surgical stapler instruments specifically adapted for use in various procedures such as end-to-end anastomosis, gastrointestinal anastomosis, endoscopic gastrointestinal anastomosis, and transverse anastomosis. Examples of stapler instruments for these various procedures can be found in U.S. Pat. Nos. 5,915,616; 6,202,914; 5,865,361; and 5,964,394, which are each herein incorporated by reference.

Known endoscopic surgical stapler instruments comprise a handle and an end effector that are fixedly attached to either ends of an elongate shaft and operatively engaged with each other. An end effector simultaneously makes a longitudinal incision in tissue and applies lines of staples on opposing sides of the incision. An end effector includes a pair of opposed jaw members that, if the instrument is intended for endoscopic or laparoscopic applications, are capable of passing through a cannula passageway. One of the jaw members, often referred to as a cartridge jaw member, receives a staple cartridge having at least two laterally spaced rows of staples in an elongate cartridge channel or a cartridge bay. The other jaw member, often referred to as an anvil jaw member, defines an anvil having staple-forming pockets aligned with the rows of staples in the staple cartridge. The instrument commonly includes a plurality of reciprocating wedges which, when driven distally, pass through openings in the staple cartridge and engage drivers supporting the staples to effect the firing of the staples toward the anvil.

In surgical stapling operation a physician operator first positions the end effector of a surgical stapler instrument to capture a target tissue between the two jaw members in open position and then operates the handle to close the two jaw members to clamp and compress the target tissue to a nominal thickness defined by the gap distance between the tissue contacting surfaces of the staple cartridge and the anvil prior to the firing of the staples. In the designs of presently available stapler instruments a physician has no means to control the degree or force of target tissue compression but is presented with a set of standardized staple cartridges colored coded according to the formed height(s) of staples contained therein, which correlates with the gap distance between the tissue contacting surfaces of the stale cartridge and anvil. Presently, the standardized set of staple cartridges, typically color coded white, blue, gold, green and black in the ascending order of staple heights contained therein, includes staples with formed heights between 1 mm and 2.3 mm in discrete increment. There are also in the market a set of staple cartridges, each cartridge containing a combination staples of varying heights with its own unique color coding tailored for application on tissue with varying compressed thickness. In compressing the target tissue the two jaw members comprising the end effector of stapler instrument are subject to a distributed reactionary load from the compressed tissue usually resulting in deflection of the two jaw members increasing progressively along the length thereof going from the proximal to distal end and more so, in the anvil than in the cartridge jaw member which is more substantial and structurally rigid. The corresponding variation in the gap distance between the tissue contacting surfaces of the staple cartridge and the anvil makes the tissue compression non-uniform decreasing progressively going from the proximal to distal ends of the end effector.

The level of tissue compression is one of the key factors that determine success of a surgical stapling operation often defined by adequate hemostasis and minimal damage of tissue along the staple line, and leak-free sealing of the target tubular organ among other considerations. It is known that a desirable clinical outcome of a surgical stapling operation is most likely achieved when the target tissue is compressed to a compression force between 6 g/mm$^2$ or 8 g/mm$^2$. Since present surgical stapler technology does not provide means to control the compression force of the target tissue a physician needs to choose a staple cartridge out of a standard set that would best approximate the optimal compression force for the target tissue when the two jaw members are closed with the chosen staple cartridge mounted in the cartridge bay. Having no practical means to help direct selection of staple cartridge, for example, accessory tools to directly assess a key mechanical property or condition of the target tissue, a physician is left to rely solely on his or her experience, or educated guess in selecting a staple cartridge, which leaves open possibility of under- or over-compression of the target tissue. Under-compression of tissue could lead to inadequate hemostasis and potential leakage of content contained within the tissue while over-compression to tearing of tissue or ischemia requiring prolonged period of healing. The staple cartridge selection is particularly difficult for a target tissue belonging to an organ with naturally occurring, large thickness variation such as in the stomach or an organ with unknown variation in mechanical properties such as in the lung at different disease state.

Manufacturers of present surgical stapler instruments instruct a physician to verify the adequacy of selected staple cartridge in compressing a target tissue by the feedback force felt in the hand operating the handle of the stapler instrument to apply the tissue compression. The instructions basically say to switch to a new staple cartridge with staples of larger formed height if it is overly difficult to operate the handle to apply compression to the target tissue specifically to guard against over-compression. This method is proven to be hardly practical in the field because the feedback force felt in the palm of the physician's hand may not necessarily correlates with the level of tissue compression due to the facts that the feedback force may be distorted being passed down through mechanical linkages and joints comprising the operating mechanism for the end effector and that the two jaw members comprising the end effector undergoes deflection caused by the reactionary load from the compressed tissue. In addition a unit of change in the compressed tissue thickness represented by the standard set of staple cartridges typically corresponds to only around few tens of gram of force in tissue compression which is barely discernible by the haptic sense felt in the palm of the hand alone even under the best of circumstances. Corresponding instruction for staple cartridge selection for preventing under-compression of a target tissue does not even exist.

U.S. Pat. No. 8,893,946 to Boudreaux et al., which is herein incorporated by reference, describes a surgical instrument that includes components for measuring the thickness of a tissue clamped between the two jaw members of an end effector thereof relying on a strain gauge or strain gauges as a means to generate a signal or signals corresponding to the tissue thickness and/or a compression load applied to the tissue. This disclosure describes the strain gauges as being used stand-alone but fails to describe how the strain gauges are practically implemented, for example, in the form of a load cell, well known to those of skill in the art, to generate such signals that could be converted to the thickness of tissue or the compression load acting thereon. The surgical instrument in this disclosure does not include any means to prevent or compensate for the potential deflection of a jaw member comprising an end effector as a result of a reactionary load from the compressed tissue nor for the effect of the play present in the closure mechanism of the two jaw members comprising the end effector on the tissue thickness measurement. This disclosure also fails to define the thickness of the clamped tissue in such sufficient detail for it to be of practical use in the selection of a staple cartridge for a stapling operation on the tissue.

Therefore, significant needs exist for a surgical device and method that would aid a physician in selecting a staple cartridge from the standard set of staple cartridges.

BRIEF SUMMARY OF THE INVENTION

The present invention is directed toward a surgical device and method for use in surgical procedures. More particularly, the present invention relates to a surgical device and method for assisting selection of a staple cartridge from the standard set of staple cartridges optimal for a target tissue of a surgical stapling operation.

To address the foregoing needs and with other objects in view there are provided, in accordance with the present invention, a surgical device for enabling a surgical stapler instrument to compress a tissue consistently to a predetermined thickness and measure a reactionary load therefrom and a method for assisting a physician in selecting a staple cartridge optimal for a tissue of a surgical stapling operation.

In a preferred embodiment of the present invention, a compression gauge cartridge for use mounted in a cartridge bay of a cartridge jaw member comprising an end effector, together with an anvil jaw member having a tissue contacting surface, of a surgical stapler instrument to compress a tissue consistently to a predetermined thickness and measure a reactionary load therefrom for assisting selection of a staple cartridge and assessing a condition of a tissue comprises: a cartridge body having a proximal end and a distal end, and a tissue supporting surface, wherein said cartridge body is configured for said compression gauge cartridge to be releasably mounted in said cartridge bay and for said tissue supporting surface to be at least at a predetermined distance from said tissue contacting surface of said anvil jaw member when said cartridge jaw member and said anvil jaw member are in a fully closed position; a force gauge assembly comprising a force transducer and a compression head having a tissue compression face, wherein said force gauge assembly is supported by said cartridge body positioned between said proximal end and said distal end thereof and wherein said compression head is configured and disposed so that said tissue compression face thereof lies substantially closer to said tissue contacting surface of said anvil jaw member than said tissue supporting surface of said cartridge body; and a spacer member extending from said tissue supporting surface of said cartridge body, wherein said compression head comprising said force gauge assembly is positioned distally with respect to said spacer member. In an alternate embodiment said tissue supporting surface of said cartridge body may be contoured in such a way to further reduce compression of said tissue disposed between said tissue supporting surface and said tissue contacting surface when said cartridge jaw member and said anvil jaw member are in a fully closed position.

In an alternate embodiment of the present invention, a compression gauge cartridge for use mounted in a cartridge bay of a cartridge jaw member comprising an end effector, together with an anvil jaw member having a tissue contacting surface, of a surgical stapler instrument to compress a tissue so that said cartridge jaw member and said anvil jaw member come to a predetermined angular positional relationship with each other and measure a reactionary load therefrom for assisting selection of a staple cartridge comprises: a cartridge body having a proximal end and a distal end, and a tissue supporting surface, wherein said cartridge body is configured for said compression gauge cartridge to be releasably mounted in said cartridge bay and for said tissue supporting surface to be at least at a predetermined distance from said tissue contacting surface of said anvil jaw member when said cartridge jaw member and said anvil jaw member are in a fully closed position; and a force gauge assembly comprising a force transducer and a compression head having a tissue compression face, wherein said force gauge assembly is supported by said cartridge body positioned between said proximal end and said distal end thereof and wherein said compression head is configured and disposed so that said tissue compression face thereof lies substantially closer to said tissue contacting surface of said anvil jaw member than said tissue supporting surface of said cartridge body. In an alternate embodiment said tissue supporting surface of said cartridge body may be contoured in such a way to further reduce compression of said tissue disposed between said tissue supporting surface and said tissue contacting surface when said cartridge jaw member and said anvil jaw member are in a fully closed position.

In an embodiment of the present invention, a surgical stapler instrument may further include a spacer block of a predetermined height disposed at a handle comprising said surgical stapler instrument for defining a predetermined extent said handle may be operated to close a cartridge jaw member and an anvil jaw member comprising an end effector comprising said surgical stapler instrument so that said cartridge jaw member and said anvil jaw member come to a predetermined angular positional relationship with each other.

In a preferred embodiment of the present invention, a surgical compression gauge instrument for compressing a tissue consistently to a predetermined thickness and measuring a reactionary load therefrom for assisting selection of a staple cartridge and assessing a condition of a tissue comprises: a handle portion; a body portion extending distally from said handle portion and defining a longitudinal axis; and a tool assembly disposed at a distal end of and operatively connected to said body portion, and comprising a compression gauge jaw member having a proximal end and a distal end and a tissue supporting surface, and an anvil jaw member having a tissue contacting surface, wherein said compression gauge jaw is configured for said tissue supporting surface thereof to be at least at a predetermined distance from said tissue contacting surface of said anvil jaw member when said compression gauge jaw member and said anvil jaw member are in a fully closed position, and configured to open and close when operated by said handle portion, wherein said compression gauge jaw member comprises a force gauge assembly, supported therein and positioned between said proximal end and said distal end thereof, comprising a force transducer and a compression head having a tissue compression face, wherein said compression head is configured and disposed so that said tissue compression face thereof lies substantially closer to said tissue contacting surface of said anvil jaw member than said tissue supporting surface of said compression gauge jaw member; and a spacer member extending from said tissue supporting surface of said compression gauge jaw member, wherein said compression head comprising said force gauge assembly is positioned distally with respect to said spacer member.

In a preferred embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from the standard set of staple cartridges containing staples of a height corresponding to said predetermined thickness of said compressed tissue if the result of comparison is case (1), or a staple cartridge containing staples of a height smaller than said predetermined thickness of said compressed tissue taking into account said size of difference if the result of comparison is case (2), or a staple cartridge containing staples of a height larger than said predetermined thickness of said compressed tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined average height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to an average height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from said standard set of staple cartridges containing staples of an average height corresponding to said predetermined thickness of said compressed tissue if the result of comparison is case (1), or a staple cartridge containing staples of an average height smaller than said predetermined thickness of said compressed tissue taking into account said size of difference if the result of comparison is case (2), or a staple cartridge containing staples of an average height larger than said predetermined thickness of said compressed tissue taking into account said size of difference if the result of comparison is case (3). In an alternate embodiment, a method for selecting a staple cartridge from the standard set of staple cartridges, each containing staples of a predetermined average height, optimal for a tissue of a surgical stapling operation may further comprise a step of waiting for a predetermined length of time after closing said cartridge jaw member and said anvil jaw member to compress said tissue.

In another alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a green cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value; selecting a green cartridge from the standard set of staple cartridges if the result of comparison is case (1) or a blue cartridge if the result of comparison is case (2), or a black cartridge if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; providing a reference tissue for which an optimal staple height for a surgical stapling operation is known; comparing said reactionary load reading with a reactionary load from said reference tissue compressed to said predetermined thickness over the same area of said reference tissue as that of said tissue compression face of said compression head to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member having a tissue contacting surface, of a surgical stapler instrument; capturing a tissue between said cartridge jaw member and said anvil jaw member; closing said cartridge jaw member and said anvil jaw member to compress said tissue captured there-between so that said cartridge jaw member and said anvil jaw member come to a predetermined angular positional relationship with each other; reading out a reactionary load from said compressed tissue displayed on a force transducer indicator; providing a reference tissue for which an optimal staple height for a surgical stapling operation is known; comparing said reactionary load reading with a reactionary load from said reference tissue compressed so that said cartridge jaw member and said anvil jaw member come to said predetermined angular positional relationship with each other to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In order to make an informed selection of a staple cartridge for a tissue of a surgical stapling operation or to assess a condition of a tissue in a surgery, a physician mounts a compression gauge cartridge of the present invention in a cartridge bay of a cartridge jaw member of a surgical stapler instrument prepared to be used for the stapling operation or employ a dedicated surgical instrument with a tool assembly, a jaw member of which is instrumented with a compression gauge device including a force gauge assembly and a spacer member. The physician then operates the handle portion of the surgical stapler instrument or the dedicated surgical instrument to capture a tissue between the two jaw members comprising the end effector or a tool assembly and close the two jaw members to compress the tissue to a predetermined thickness set by the spacer member comprising the compression gauge cartridge or the compression gauge device. The surgical stapler instrument instrumented with the compression gauge cartridge and the dedicated surgical instrument instrumented with the compression gauge device is capable of providing a predetermined gap distance consistently and with a high degree of repeatability between the tissue compression face of the compression head comprising the force gauge assembly and the tissue contacting surface of the anvil jaw member. The compression of tissue takes place over the area covered by the tissue compression face of the compression head, which reduces the tissue to a predetermined thickness corresponding to the predetermined gap distance. Preferably, the predetermined thickness of the compressed tissue is the formed height of staples contained in a green staple cartridge from the standard set of staple cartridges. The compression head transfer a reactionary load from the compressed tissue exerted thereon to the force transducer comprising the force gauge assembly, which is displayed on a force transducer indicator connected to the force transducer comprising the force gauge assembly. Comparing the reactionary load with a known optimal tissue compression force for a surgical stapling operation the physician may decide to choose a green staple cartridge or other staple cartridges, blue or black, containing staples of a height smaller or larger than the green cartridge in the standard set of staple cartridges. Preferably, the control program for the force transducer indicator includes a software function for performing the comparison of the measured reactionary load with a set of values stored in the internal memory to provide a signal indicating a recommendation on the staple cartridge selection, for example, in the form of a color coded signal lights or other easily recognizable forms.

The presently disclosed compression gauge cartridge and method, together with attendant advantages, will be more clearly illustrated below by the description of the drawings and the detailed description of the embodiments.

BRIEF DESCRIPTION OF THE DRAWINGS

The following exemplary figures are provided to supplement the description below and more clearly describe the invention. In the figures, like elements are generally designated with the same reference numeral for illustrative convenience and should not be used to limit the scope of the present invention.

DETAILED DESCRIPTION OF THE INVENTION

Figure 1:
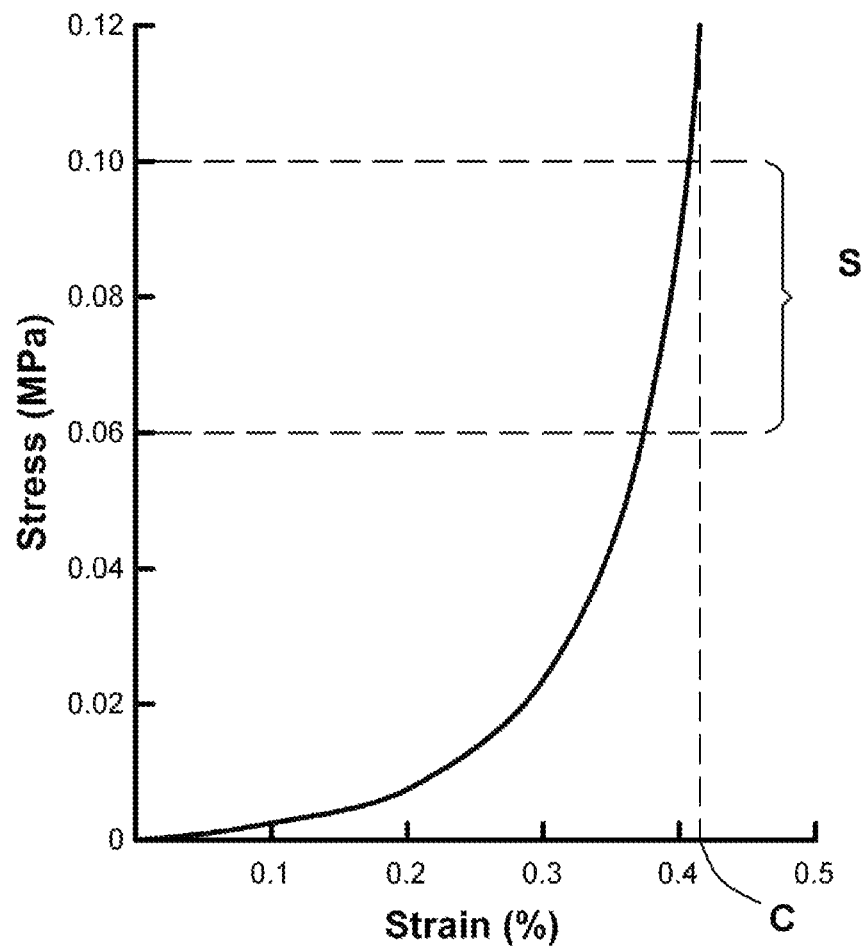
FIG. 1 is a plot of a stress-strain curve of a stomach tissue according to an embodiment of the present invention.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

Embodiments of the presently disclosed surgical device will now be described in detail with reference to the drawing figures wherein like reference numerals identify similar or identical elements. In the drawings and in the description which follows, the term "proximal", as is traditional, will refer to the end of the surgical device which is closest to a physician while the term "distal" will refer to the end of the device which is furthest from a physician. However, surgical instruments are used in many orientations and positions, and these terms are not intended to be limiting and absolute. The terms "force", "load", and "force load" may be used interchangeably herein to describe various mechanical forces including a reaction thereto. It should be appreciated that spatial terms such as vertical, horizontal, right, left or above, etc., are given herein with reference to the figures. In actual practice, however, a surgical device or instrument may be oriented at various angles and, as such, these spatial terms are used relative to the surgical device or instrument.

The present invention relates to a surgical device and method for use in a surgical procedure. More particularly, the present invention relates to a surgical device for enabling compression of a tissue consistently to a predetermined thickness with a high degree of repeatability and measurement of a reactionary load from the compressed tissue to assist in the selection of a staple cartridge from the standard set of staple cartridges optimal for the tissue of a surgical stapling operation and to assess a condition of a tissue of a surgical operation in a surgical procedure. In an embodiment a surgical device of the present invention may be advantageously adapted for use, as an add-on accessory, mounted in a cartridge bay comprising a cartridge jaw member of an end effector of an endoscopic surgical stapler instrument. A surgical device of the present invention may be configured to include retention features similar to a staple cartridge for releasably mounting in an open cartridge bay, if available in a surgical stapler instrument, or otherwise fixedly integrated with a cartridge jaw member of a disposable reload unit found in certain surgical stapler instruments in the market. Advantages of a surgical device of the present invention implemented as an add-on accessory to existing surgical stapler instrument include a reduced cost of use and ease of use to a physician who is already familiar with the operation of such surgical stapler instrument. In an alternate embodiment a surgical device of the present invention may be integrated with or configured as an add-on accessory to a surgical instrument dedicated to implementation of the capabilities offered by a surgical device of the present invention, which may generally comprise two opposing jaw members comprising a tool assembly, corresponding to an end effector of a surgical stapler instrument, fixedly and operably attached to a handle assembly via an elongate body and configured to open and close when operated by the handle assembly. Although the implementation and operation of a surgical device in various embodiments of the present invention will be described in the following as it relates to a endoscopic surgical stapler instrument and endoscopic surgical instrument, it should be apparent to those of skill in the art that the aspects of the present disclosure may be readily adapted for use with other surgical stapler instruments as well as other types of surgical instruments.

The present invention is being discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is to be understood that the present invention may find use in any procedure where access is limited to a small incision, including but not limited to laparoscopic procedures, as well as open procedures.

The characteristic behavior of a tissue undergoing deformation under external stress load, for example, a compressive stress load applied by a pair of jaw members comprising an end effector of a surgical stapler instrument, has been widely studied (for example, Jacob Rosen et. al., "Biomechanical Properties of Abdominal Organs In Vivo and Postmortem Under Compression Loads," Journal of Biomedical Engineering, Vol. 130, pp. 1-17) and is generally represented by a stress-strain curve plot, well known to those of skill in the art, shown in FIG. 1 in an exemplary representation for a stomach tissue. In response to a compressive stress load, depicted in the vertical axis of the plot, the stomach tissue undergoes a rapid deformation, represented as strain, defined as a percentile reduction in tissue thickness, and depicted in the horizontal axis of the plot, in response to a relatively small change in the compressive stress load at the lower level thereof. At the higher level the stress-strain curve becomes close to a line indicating a linear elastic behavior of the stomach tissue characterized by an elastic modulus defined as the largely constant slope of the stress-strain curve. This general characteristic behavior of a stomach tissue as well as other bodily tissue under a compressive stress load is often described as a viscoelastic behavior, by those of skill in the art, exhibiting typical characteristics of both a viscous liquid and an elastic solid subject to an external compressive stress load. The initial rapid deformation of the stomach tissue at the lower level of compressive stress load is largely due to initial displacement of viscous, liquid-like components of the tissue causing a rapid reduction in thickness of the tissue under a relatively weak compressive stress load applied to an area thereof. The elastic response of the tissue at the higher level of compressive stress load is largely due to relatively immobile fibrous, solid-like components of the tissue responding to the compressive stress load collectively with substantially elastic behavior. At further higher up in the compressive stress load level the strain of the tissue reaches what is known to those of skill in the art as the ultimate tensile strength or the breaking point, labeled with a letter C in FIG. 1 where the internal structure of the tissue starts to break down and eventually completely loses ability to recoverably respond to an additional compressive stress load.

The almost linear correlation between the stress and strain of a stomach tissue and, to an extent, similar behavior exhibited in other bodily tissues at the compressive stress load interval of interest, particularly, as it relates to a surgical stapling operation, indicated by a bracket labeled with a letter S in FIG. 1, makes it possible to infer the change in the compressive stress load acting on the stomach tissue if the change in the thickness of the stomach tissue resulting therefrom is known and vice versa. Based on this observation, one could devise a practical scheme for the selection of a staple cartridge, containing staples of optimal height for a tissue of a surgical stapling operation, from the standard set of staple cartridges, which generally include steps of compressing a tissue to a predetermined thickness, i.e., to a predetermined strain; measuring a compressive stress load, i.e., a reactionary load from the compressed tissue, required to cause such reduction in thickness; comparing the measured compressive stress load to the known optimal value for a surgical stapling operation, for example, 8 $g/mm^2$ as previously described in the BACKGROUND, noting the size of difference between the measured compressive stress load and the optimal value; and based on the result of comparison, deciding whether to select a staple cartridge with staples of formed height closest to the compressed tissue thickness or of different formed heights taking into account the size of difference, i.e., change the strain induced on the tissue to a direction and level to modify the compressive stress load exerted on the tissue to be closer to the optimal value. As will be described in detail hereinafter, implementation of such a scheme on a platform of existing surgical instrument, particularly, a surgical stapler instrument may heavily rely on being able to methodically constrain the closure of the two jaw members comprising an end effector or a tool assembly to compress a tissue consistently to a predetermined thickness with a high degree of repeatability and to measure a reactionary load from the compressed tissue.

Figure 2A:
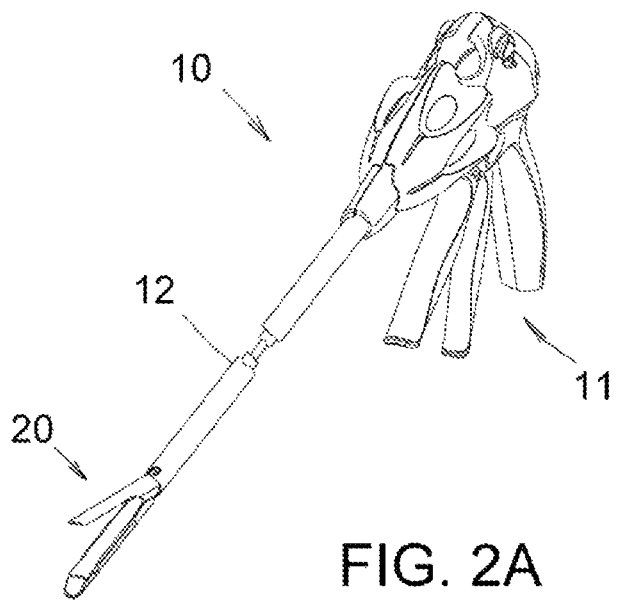
FIG. 2A is a perspective view of an exemplary surgical stapler instrument according to an embodiment of the present invention.
Figure 2B:
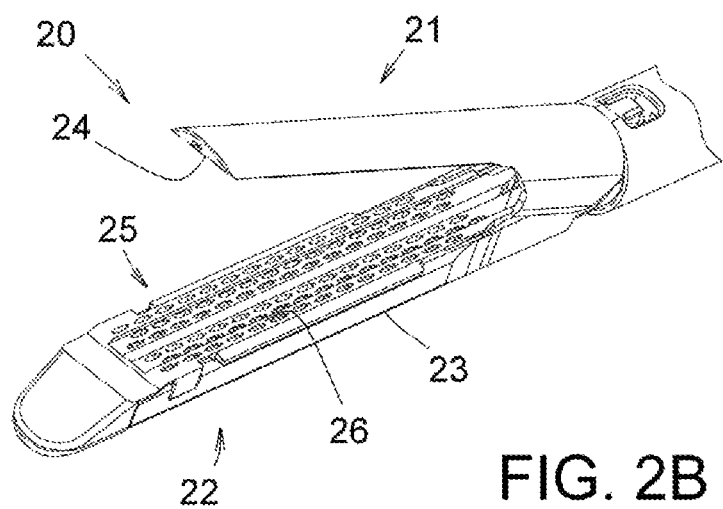
FIG. 2B is a perspective view of an end effector of an exemplary surgical stapler instrument according to an embodiment of the present invention.

Referring to FIGS. 2A and 2B, an exemplary surgical stapler instrument 10 and an enlarged view of an end effector 20 thereof are shown. Surgical stapling instrument 10 includes a handle assembly 11, end effector 20 and an elongate tube 12 that operatively connects handle assembly 11 and end effector 20 through a drive mechanism (not shown in the FIGURES). End effector 20 comprises a first jaw member 21 and a second jaw member 22. Second jaw member 22 comprises an elongate channel 23, sometimes referred to as a cartridge bay, configured to receive a staple cartridge 25 having a tissue contacting surface 26. First jaw member 21 comprises an anvil having a tissue contacting surface 24 that is aligned and pivotally engaged through a pivot mechanism (not shown) with second jaw member 22 forming a pair of opposed jaw members that open and close, when driven by the drive mechanism operated with handle assembly 11 by a physician, to capture and compress a tissue there-between for stapling. Various different drive mechanisms, well known to those of skill in the art, are employed to actuate a pivot mechanism joining two jaw members 21, 22 to cause opening and closing thereof including a drive pin and cam groove mechanism, reciprocating closure tube assemblies, gear mechanisms, rack and pinion mechanism, and pulley mechanism, etc. Typically, handle assembly 11 driving end effector 20 is configured in such a way that first and second jaw members 21, 22 are capable of rigidly holding their approximated positional relationship, i.e., a locked position, when closed to capture and compress the tissue prior to the deployment and formation of staples. Those of skill in the art would appreciate that the exemplary surgical stapler instrument depicted in the FIGURES comprises one surgical stapler instrument version with which various embodiments of a surgical device of the present invention may be advantageously employed.

The pivotal engagement between two jaw members 21, 22 comprising an end effector 20 may take various configurations including a hinge about which two jaw members 21, 22 are configured to rotate and a cam groove along which a drive pin is configured to translate to open or close end effector 20. The clearances built in the mechanical designs of the pivot mechanism and the drive mechanism to ensure smooth operations thereof and, to a lesser extent, unavoidable manufacturing tolerances in the parts thereof inevitably introduce a measurable play in the pivotal motion of two jaw members 21, 22, which manifests as an inherent uncertainty in the positional relationship between two jaw members 21, 22, particularly, in the relative angular position thereof even under unloaded condition, that is, without a tissue captured and compressed there-between. Of particular significance to a device and method in an embodiment of the present invention is a variation in the relative angular position of the two jaw members that may be appropriately referred as a backlash, i.e., a tendency for the closed jaw members to open back up, the size of which is strongly dependent on the level of compression of a tissue there-between. The variation in the backlash introduces, in effect, variability in the gap distance, defined as a distance between tissue contacting surfaces 24, 26, of two jaw members 21, 22 at a given position along the length of end effector 20, which also varies with the size of a reactionary load from the compressed tissue. The uncertainty in the gap distance due to the play in the pivot mechanism tends to become more pronounced going farther away distally from pivot mechanism due to a lever arm effect. A reactionary load from the compressed tissue acting on two jaw members 21, 22 may add to variability in the gap distance by potentially causing a deformation or a deflection of two jaw members 21, 22, more likely, an anvil the less stiffer of the two, the degree of which differs depending the size of the reactionary load and, therefore, is not easy to estimate or measure. In practice, the gap distance has been observed to vary very significantly from one tissue to another mostly due to the deflection of the anvil, irrespective of particular brands of surgical stapler instrument in the market, and in fact, there are no dedicated mechanisms implemented on the existing surgical stapler instrument products to precisely and actively control the gap distance during compression of a tissue. Instead, when critically needed, for example, in case of a very thick tissue, an external constraining means is employed to control the gap distance to some extent in certain surgical stapler instruments in the market. For this reason, a surgical stapler instrument presently being marketed does not make a suitable platform on which to implement the staple cartridge selection scheme, described previously, which hinges on an ability to compress a tissue consistently to a well defined thickness and measure a reactionary load therefrom. A surgical device and method proposed in this disclosure seeks to remedy such deficiencies in a surgical stapler instrument or a new surgical instrument dedicated for implementation of such a scheme with a mechanical and operational configuration similar to those of a surgical stapler instrument without requiring a radical redesign of the instruments by providing relatively simple features that are added-on to help bring under control the variability in the gap distance between the two jaw members comprising an end effector or a tool assembly and to introduce a capability to the instruments to measure a reactionary load from the compressed tissue as will be described hereinafter.

Figure 3A:
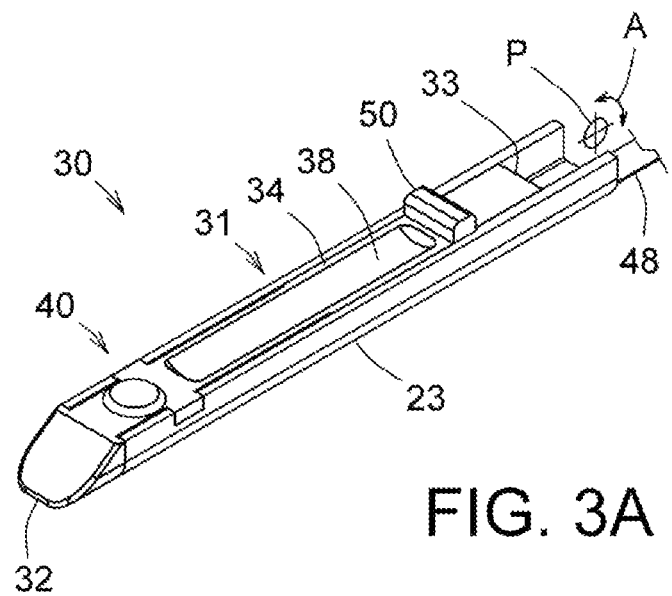
FIG. 3A is a perspective view of a compression gauge cartridge disposed in a cartridge bay of a cartridge jaw member of an end effector of an exemplary surgical stapler instrument according to an embodiment of the present invention.
Figure 3B:
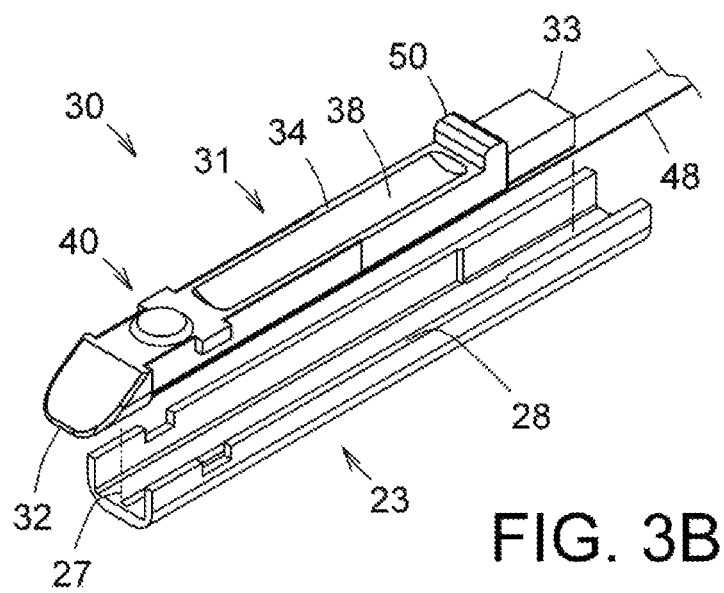
FIG. 3B is a perspective view of a compression gauge cartridge positioned spaced apart from a cartridge bay according to an embodiment of the present invention.
Figure 3C:
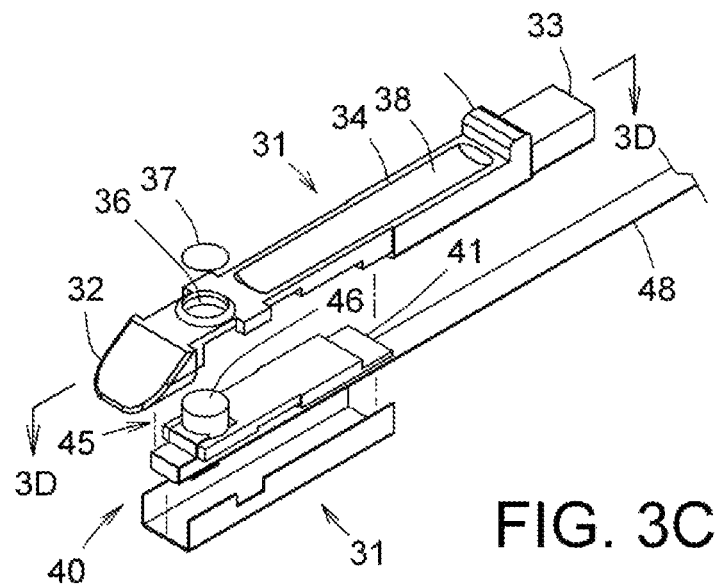
FIG. 3C is an exploded view of a compression gauge cartridge according to an embodiment of the present invention.
Figure 3D:
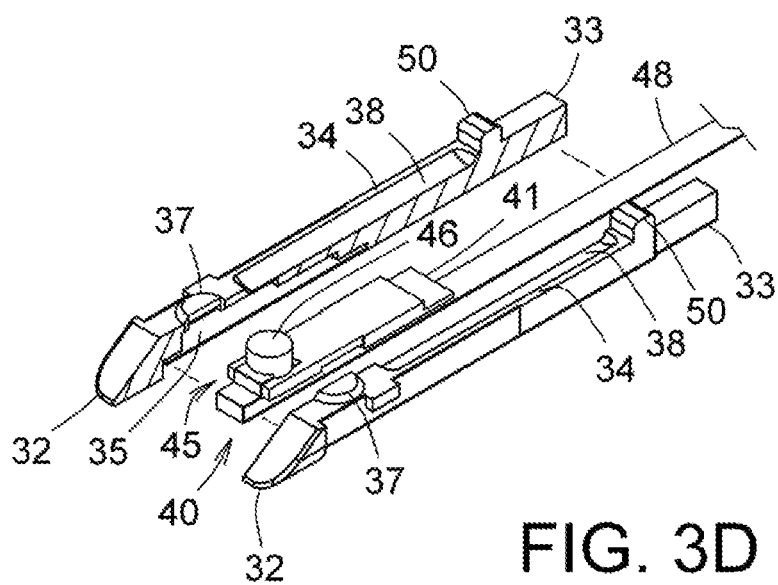
FIG. 3D is a perspective view of a compression gauge cartridge with a cartridge body sectioned along the line 3D-3D shown in FIG. 3C and spaced apart according to an embodiment of the present invention.

Referring to FIG. 3A, a compression gauge cartridge 30 is shown, in a perspective view, mounted in cartridge bay 23 of cartridge jaw member 22 of end effector 20 of surgical stapler instrument 10, as shown in FIGS. 2A and 2B, for compressing a tissue consistently to a predetermined thickness and measuring a reactionary load therefrom in an embodiment of the present invention. Anvil jaw member 21 is omitted for clarity in FIG. 3A and a pivot mechanism joining the two jaw members 21, 22 is schematically represented by a symbol labeled with a letter P and a pivotal motion by a double headed, curved arrow labeled with a letter A. In FIG. 3B compression gauge cartridge 30 is shown released from cartridge bay 23. Referring to FIG. 3C, details of construction of compression gauge cartridge 30 is shown in an exploded view in an embodiment of the present invention. In a preferred embodiment of the present invention, compression gauge cartridge 30 for use mounted in cartridge bay 23 of cartridge jaw member 22 comprising end effector 20 of surgical stapler instrument 10, together with anvil jaw member 21 having a tissue contacting surface 24, to compress a tissue consistently to a predetermined thickness and measure a reactionary load therefrom for assisting in selection of a staple cartridge optimal for a tissue of a surgical stapling operation and assessing a condition of a tissue of a surgical operation comprises: a cartridge body 31 having a proximal end 32 and a distal end 33, and a tissue supporting surface 34 corresponding to tissue contacting surface 26 of staple cartridge 25, wherein cartridge body 31 may be configured for compression gauge cartridge 30 to be releasably mounted in cartridge bay 23 and for tissue supporting surface 34 to be at least at a predetermined distance from tissue contacting surface 24 of anvil jaw member 21 when cartridge jaw member 22 and anvil jaw member 21 are in a fully closed position; a force gauge assembly 40 comprising a force transducer 41 and a compression head 45 having a tissue compression face 46, wherein force gauge assembly 40 may be supported by cartridge body 31 positioned between proximal end 32 and distal end 33 thereof, and wherein compression head 45 comprising said force gauge assembly 40 may be configured and disposed so that tissue compression face 46 thereof may lie substantially closer to tissue contacting surface 24 of anvil jaw member 21 than tissue supporting surface 34 of cartridge body 31; and a spacer member 50 extending from tissue supporting surface 34 of said cartridge body 31, wherein force gauge assembly 40 may be positioned distally with respect to spacer member 50. In an alternate embodiment tissue supporting surface 34 of cartridge body 31 may be contoured in such a way to further reduce compression of a tissue disposed between tissue supporting surface 34 and tissue contacting surface 21 when cartridge jaw member 22 and anvil jaw member 21 are in a fully closed position. Further details of compression gauge cartridge 30 can be seen in FIG. 3D showing, in a perspective view, cartridge body 31 sectioned along the line 3D-3D shown in FIG. 3C and spaced apart in an embodiment of the present invention. As will become more clear with the following description, compression gauge cartridge 30 is configured to allow an existing surgical stapler instrument to be used without modification in applying a compression to a predetermined area of a tissue captured between the two jaw members comprising an end effector thereof consistently and with a high degree of repeatability to a predetermined thickness substantially free of variations of mechanical and structural origins and measuring a reactionary load from the compressed area of the tissue dynamically throughout the compression operation. In an embodiment of the present invention cartridge body 31 comprising compression gauge cartridge 30 may be configured for compression gauge cartridge 30 to be releasably mounted and securely retained in cartridge bay 23 comprising cartridge jaw member 22 of end effector 20. In an alternate embodiment cartridge body 31 comprising compression gauge cartridge 30 may be configured to be fixedly mounted in cartridge bay 23 to be integrated with cartridge jaw member 22 of end effector 20 of surgical stapler instrument 10. In another alternate embodiment cartridge body 31 comprising compression gauge cartridge 30 may be configured to be fixedly mounted in a cartridge bay to be integrated with a cartridge jaw member of an end effector comprising a disposable reload unit of a certain surgical stapler instrument product in the market.

Figure 4A:
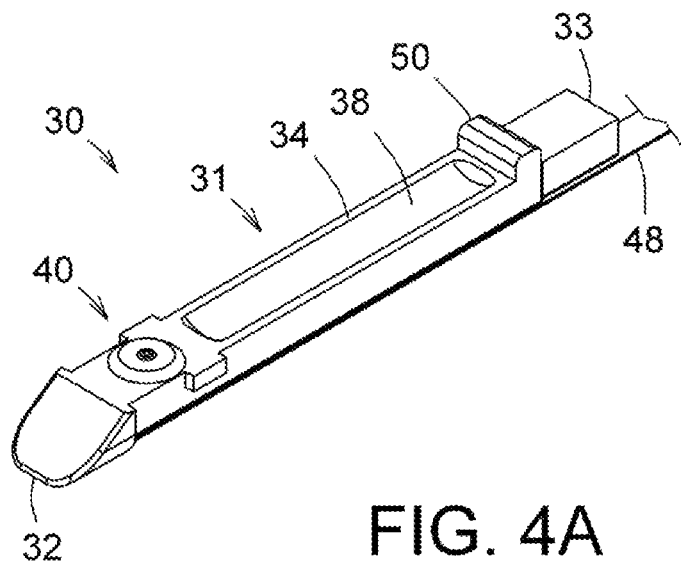
FIG. 4A is a perspective view of a compression gauge cartridge according to an alternate embodiment of the present invention.
Figure 4B:
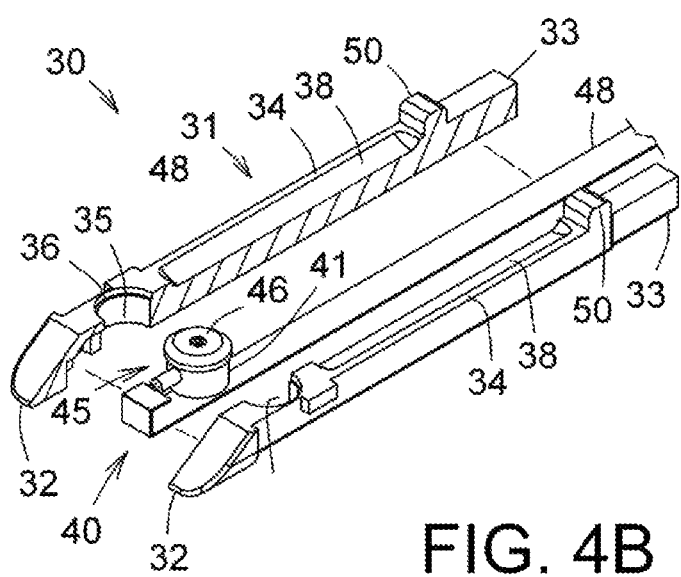
FIG. 4B is a perspective view of a compression gauge cartridge, shown in FIG. 4A, with a cartridge body sectioned similarly to that shown in FIG. 3C and spaced apart according to an alternate embodiment of the present invention.
Figure 5A:
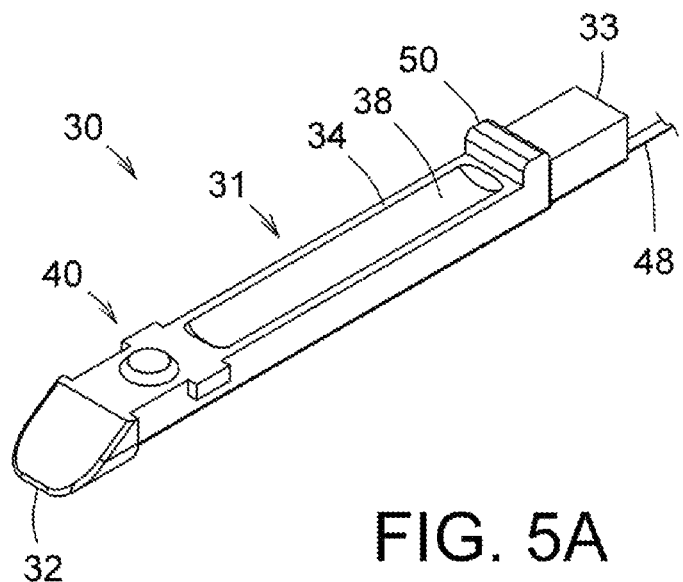
FIG. 5A is a perspective view of a compression gauge cartridge according to another alternate embodiment of the present invention.
Figure 5B:
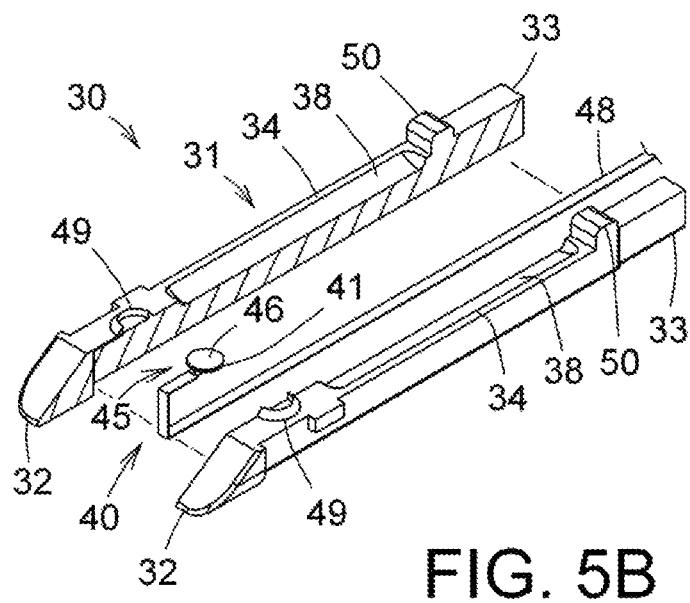
FIG. 5B is a perspective view of a compression gauge cartridge, shown in FIG. 5A, with a cartridge body sectioned similarly to that shown in FIG. 3C and spaced apart according to another alternate embodiment of the present invention.

Referring to FIGS. 3A-3D force transducer 41 comprising force gauge assembly 40 is depicted as having a configuration of a beam supported by cartridge body 31 housed in a cavity 35 therein in an embodiment of the present invention. In an alternate embodiment force transducer 41 comprising force gauge assembly 40 may have a configuration of a button supported by cartridge body 31 housed in a cavity 35 therein as shown in FIGS. 4A and 4B in similar arrangements to FIGS. 3A and 3D, respectively. In another alternate embodiment force transducer 41 comprising force gauge assembly 40 may have a substantially planar configuration supported by cartridge body 31 disposed on tissue supporting surface 34 thereof as shown in FIGS. 5A and 5B in similar arrangements to FIGS. 3A and 3D, respectively. In various embodiments of the present invention cartridge body 31 comprising compression gauge cartridge 30 provides a structurally stable platform upon which force transducer 41 relies in performing a force measurement operation exerted thereon. More detailed descriptions will follow hereinafter in a section dedicated to the force transducer.

In an embodiment of the present invention cartridge body 31 comprising compression gauge cartridge 30 may be configured to include selected design features similar to those found in a conventional staple cartridge that allow a conventional staple cartridge to be releasably mounted and securely retained in a cartridge bay of a cartridge jaw member during a stapling operation. In an alternate embodiment cartridge body 31 may include additional design features for releasable mounting and secure retention thereof in a cartridge bay and safety features for safe and effective use of a surgical stapler instrument instrumented with compression gauge cartridge 30 by a physician with average level of experience and skill in use of an ordinary surgical stapler instrument. In an embodiment, materials and method of manufacture substantially similar to those used to construct a conventional staple cartridge may be employed and appropriately adapted to manufacture cartridge body 31 comprising compression gauge cartridge 30. In an alternate embodiment cartridge body 31 may include structural reinforcements and/or unconventional construction materials, not ordinarily found in a conventional staple cartridge, to ensure proper operation of force gauge assembly 40 comprising compression gauge cartridge 30 and compression of a tissue in cooperation with an anvil jaw member comprising an end effector. As will be described hereinafter, the distribution of a reactionary load on cartridge body 31 from a tissue under compression in operation of surgical stapler instrument 10 instrumented with compression gauge cartridge 30 may be different, by design, from that on a conventional staple cartridge mounted in a cartridge bay of the same or comparable surgical stapler instrument in an embodiment of the present invention.

Referring to back FIGS. 3C and 3D, in an embodiment of the present invention cartridge body 31 may be configured to support force gauge assembly 40 in an open cavity 35 defined therein with an opening 36 disposed on tissue supporting surface 34 interconnecting cavity 35 and an external space above tissue supporting surface 34, through which compression head 45 comprising force gauge assembly 40 is disposed. In an embodiment opening 36 may be hermetically capped with a seal member 37 to prevent introduction of unwanted contaminant, such as bodily fluid, into cavity 35. Seal member 37 may be configured to be in contact with tissue compression face 46 of compression head 45 and provided with sufficient flexibility or, otherwise, a freedom of movement to allow displacement of compression head 45 in response to a load exerted thereto from a compressed tissue to take place substantially freely, which is generally very small and required in a normal operation of force transducer 41, as will be described later in a dedicated section. In an alternate embodiment seal member 37 may be integrated with compression head 45 on tissue compression face 46 thereof to substantially freely move concurrently therewith. In an embodiment cavity 35 may be configured, preferably, to substantially rigidly hold a stationary portion of force transducer 41 of a beam configuration to provide a structural support necessary for optimal operation thereof and to leave sufficient space to ensure unobstructed deflection of a deflectable portion of force transducer 41 and compression head engaged therewith, which is a key aspect of force measurement operation of a force transducer of a beam configuration, as is well known to those of skill in the art. Referring to FIG. 4B, in an embodiment of the present invention cavity 35 may be configured to accommodate to rigidly hold force transducer 41 of a button configuration and leave sufficient space for free movement of compression head 45 engaged therewith. In a further embodiment cartridge body 31 may be configured to support force gauge assembly 40 of a planar configuration substantially on tissue supporting surface 34 as shown in FIGS. 5A and 5B. In an embodiment a retention feature 49 may be provided to securely position force gauge assembly 40 on tissue supporting surface 34.

Figure 6A:
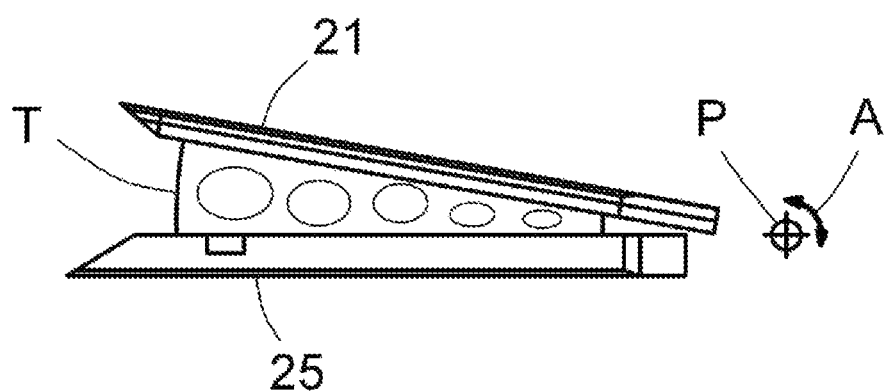
FIG. 6A is a schematic, side elevation view of a tissue captured between an anvil jaw member and a staple cartridge comprising a cartridge jaw member in an open position according to an embodiment of the present invention.
Figure 6B:
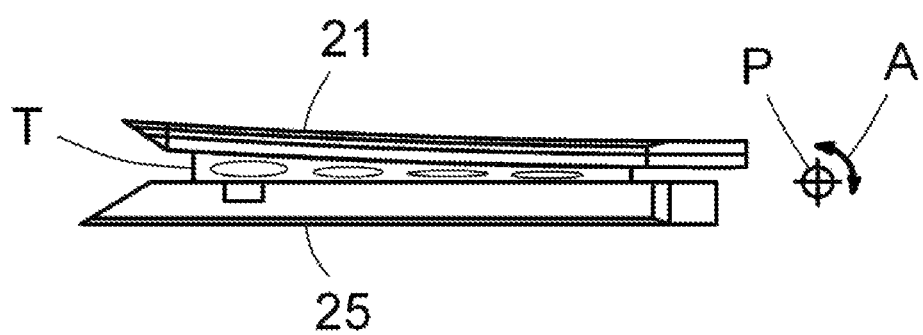
FIG. 6B is a schematic, side elevation view of a tissue compressed between an anvil jaw member and a staple cartridge in a closed position according to an embodiment of the present invention.

Referring to FIGS. 6A and 6B, schematically showing a tissue T captured and compressed, respectively, between anvil jaw member 21 and a conventional staple cartridge 25 representing a cartridge jaw member 22 as shown in FIG. 2B, the distributed reactionary load from compressed tissue T over the length of anvil jaw member 21 comprising end effector 20 often causes anvil jaw member 21 to deflect to a substantial degree typically being less stiffer than cartridge jaw member 22 instrumented with staple cartridge 25. The extent, to which anvil jaw member 21 deflects, strongly depends on the degree of compression of tissue T and gradually increases as one goes distally along the length of end effector 20 from pivot mechanism P due to a cumulative nature of the reactionary load from compressed tissue T. This is a major reason why it is not practically possible to controllably compress a tissue consistently to a known thickness with existing surgical stapler instrument mounted with a conventional stapler cartridge in a cartridge jaw member thereof in addition the inevitable plays in the pivot and drive mechanisms.

Figure 6C:
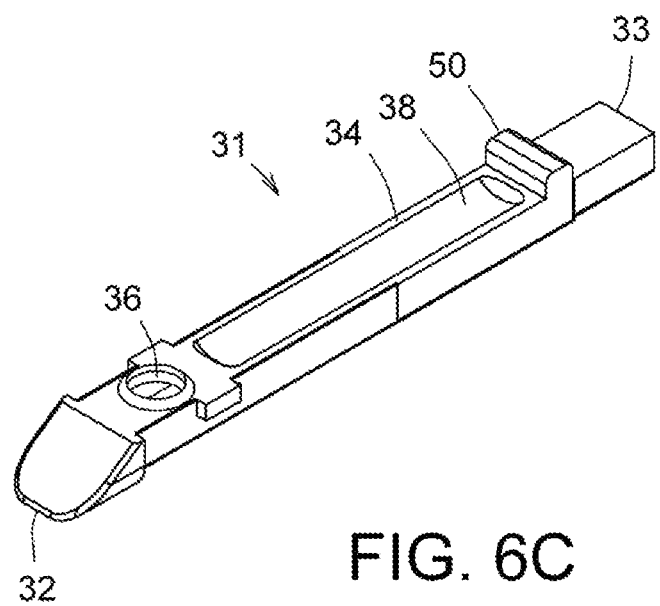
FIG. 6C is a perspective view of a cartridge body comprising a compression gauge cartridge according to an embodiment of the present invention.

With a view to substantially eliminate incontrollable deflection of an anvil jaw member, comprising an end effector together with a cartridge jaw member instrumented with a compression gauge cartridge, in performing tissue compression captured there-between, in an embodiment of the present invention, cartridge body 31, as shown in FIG. 6C in a perspective view, may be configured so that tissue supporting surface 34 thereof may be at the minimum at a predetermined distance from a tissue contacting surface of an anvil jaw member when a cartridge jaw member and an anvil jaw member are in a fully closed position with or without a tissue captured and compressed there-between. Preferably, the gap distance, defined as a distance between tissue supporting face 34 and the tissue contacting surface of an anvil jaw member, at a position along the length of the end effector may be substantially larger than the largest gap distance provided by any one from the standard set of staple cartridges at the same position and under the same loading condition from the compressed tissue, if present, so that compression of a tissue disposed over an area covered by tissue supporting surface 34 may be minimized to substantially eliminate a distributed reactionary load acting on the anvil jaw member. In an embodiment tissue supporting surface 34 may include surface contours such as a recess 38 in order to further reduce compression applied to a tissue in contact therewith. The need to keep the tissue compression under control over the area of tissue supporting surface 34 must be balanced against the requirement for the structural stiffness of a cartridge jaw member to guard against deformation thereof. Referring back to FIG. 3B, in an embodiment of the present invention cartridge body 31 may be configured for tissue supporting surface 34 thereof to lie substantially even with a top portion 28 of cartridge bay 23. In an alternate embodiment, cartridge body 31 may be configured for tissue supporting surface 34 thereof to lie substantially above top portion 28. In another alternate embodiment, cartridge body 31 may be configured for tissue supporting surface 34 thereof to lie substantially below top portion 28.

Figure 6D:
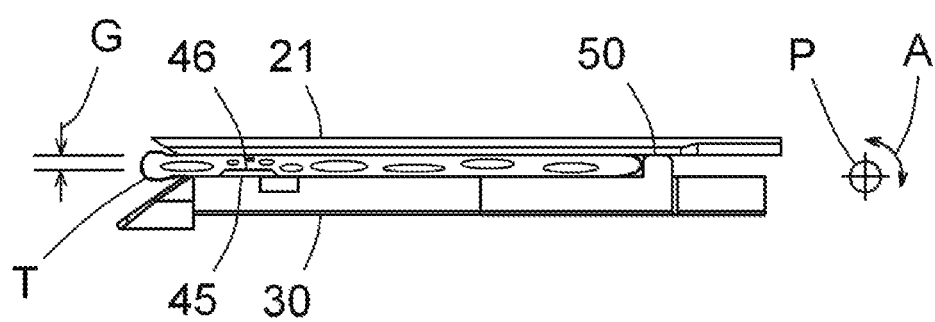
FIG. 6D is a schematic, side elevation view of a tissue compressed between a compression gauge cartridge comprising a cartridge jaw member and an anvil jaw member in a closed position according to an embodiment of the present invention.
Figure 6E:
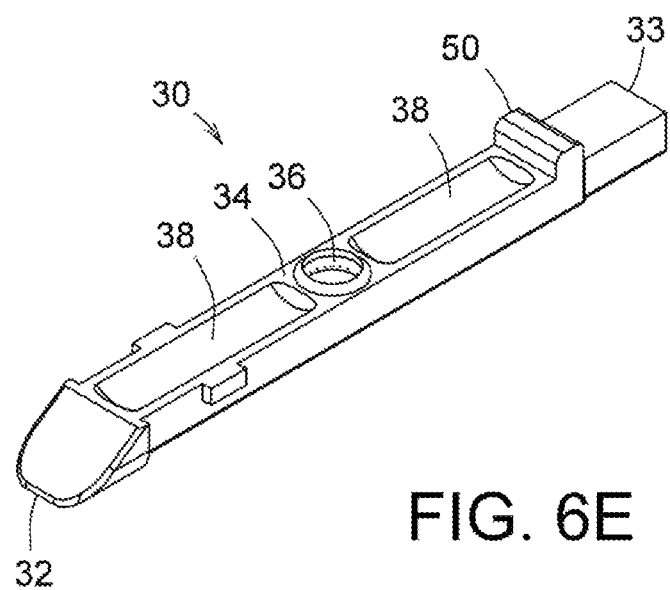
FIG. 6E is a perspective view of a cartridge body comprising a compression gauge cartridge according to an alternate embodiment of the present invention.

Located at a predetermined position along the length of cartridge body 31 on tissue supporting surface 34 thereof is an opening 36, as shown in FIGS. 3C, 3D and 4B, in an embodiment of the present invention, through which compression head 45 comprising force gauge assembly 40 is disposed. In an alternate embodiment, as shown in FIGS. 5A and 5B, force gauge assembly 40 comprising force transducer 41 of a planar configuration and compression head 45 may be disposed at a predetermined position along the length of cartridge body 31 on tissue supporting surface 34. In a preferred embodiment of the present invention compression head 45 comprising force gauge assembly 40 may be configured and disposed with respect to cartridge body 31 so that tissue compression face 46 thereof lie substantially above tissue supporting surface 34 of cartridge body 31 and closer to tissue contacting surface 24 of anvil jaw member 21, as shown in FIG. 2B, than tissue supporting surface 34 of cartridge body 31 when cartridge jaw member 22 and anvil jaw member 21 are in a fully closed position. Under such configuration, a tissue captured between a compression gauge cartridge mounted in a cartridge bay of a cartridge jaw member and an anvil jaw member experiences compression substantially exclusively over the area covered by tissue compression face 46 when two jaw members are in a fully closed position, as schematically illustrated in FIG. 6D in an embodiment, where a predetermined gap distance over tissue compression face 46 or a predetermined thickness to which a tissue is compressed is labeled by a letter G. In an embodiment of the present invention the area covered tissue compression face 46 may be varied in order to control a reactionary load from a tissue compressed thereon and substantially eliminate potential deflection of an anvil jaw member resulting therefrom. In an alternate embodiment, the position along the length of the end effector of compression head 45 comprising force gauge assembly may be varied to control a lever arm effect, as previously described, of a reactionary load from a tissue compressed thereon and substantially eliminate potential deflection of an anvil jaw member resulting therefrom as schematically shown in FIG. 6E. In another alternate embodiment, the area of tissue compression face 46 and the position along the length of the end effector of compression head 45 may be jointly varied.

Figure 7A:
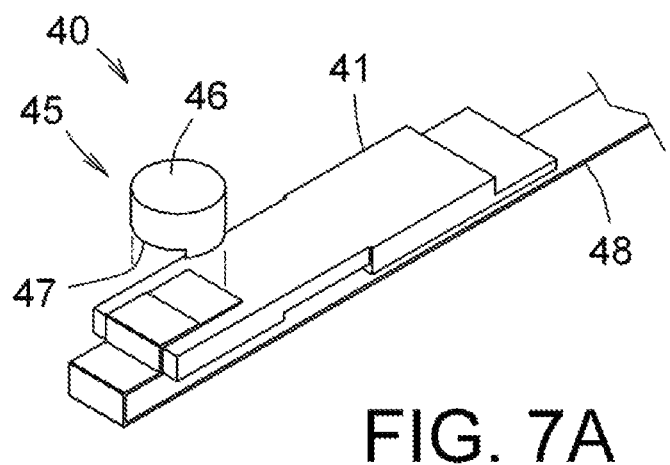
FIG. 7A is a perspective view of a force gauge assembly with a compression head set spaced apart according to an embodiment of the present invention.
Figure 8A:
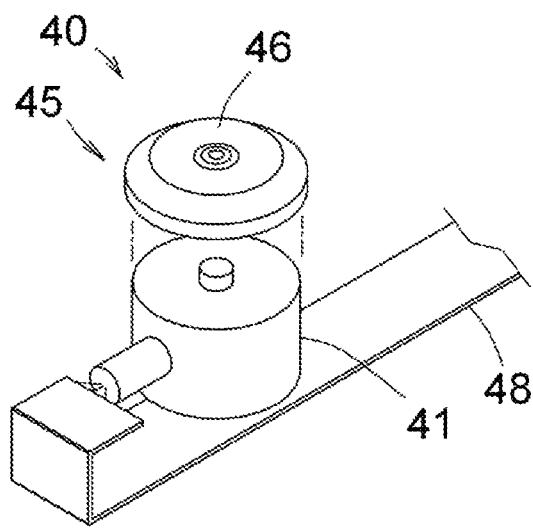
FIG. 8A is a perspective view of a force gauge assembly with a compression head set spaced apart therefrom according to an alternate embodiment of the present invention.
Figure 9A:
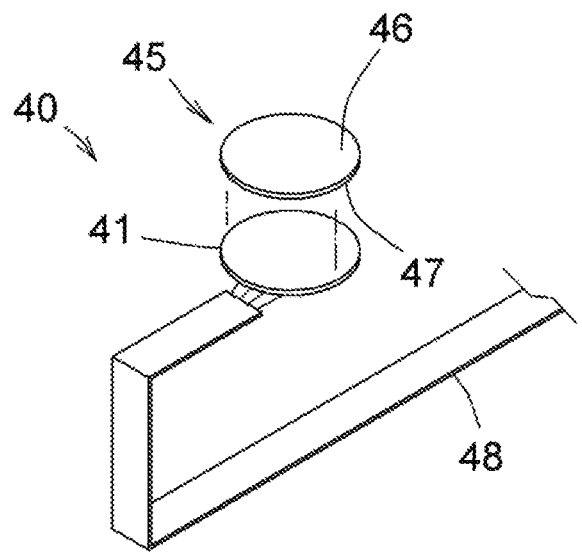
FIG. 9A is a perspective view of a force gauge assembly with a compression head set spaced apart therefrom according to another alternate embodiment of the present invention.

Referring to FIGS. 3C-4B and FIGS. 7A and 8A showing, in a perspective view, a force gauge assembly 40 comprising force transducer 41 and compression head 45 where compression head 45 is shown spaced apart from force transducer 41, in an embodiment of the present invention, force gauge assembly 40 may be disposed for compression head 45 to be located at a predetermined position along the length of cartridge body 31 between proximal end 33 and distal end 32 thereof to provide a measurement of a reactionary load from a tissue compressed in a gap between a tissue contacting surface of an anvil jaw member and tissue compression face 46 of compression head 45. In a preferred embodiment force transducer 41 may be a strain gauge based load cell of various configurations capable of generating an electrical signal when stimulated including load cells of a beam configuration including, for example, a cantilever bending beam and a parallel bending beam, as schematically illustrated in FIG. 7A, and of a button configuration, as schematically illustrated in FIG. 8A, as are well known to those of skill in the art. Strain gauge based load cells are widely available from a multitude of vendors at relatively low price levels due to their wide spread uses in industrial applications and consumer weight measurement equipments such as personal and kitchen electronic scales. In an embodiment of the present invention there is provided a signal conduction means 48 electrically connected to force transducer 41 for conducting a signal therefrom to a force transducer indicator or a controller (not shown in the FIGURES) disposed remotely from the surgical site, for example, external to a surgery patient. Appropriate signal conduction means 48 for a strain gauge based load cell and other types of load cell generating an electric signal includes a flexible flat cable and thin gauge electrical wires, both of which are widely available commercially at low cost and of such a small thickness to be able to freely pass through an annular gap between an elongate tube of a surgical stapler instrument and the inside wall of a trocar through which the instrument is deployed. In an alternate embodiment force transducer 41 may be a load cell of a planar configuration, as schematically illustrated in FIG. 9A, including a hydraulic load cell capable of generating a fluid pressure signal when stimulated, a piezoelectric load cell capable of generating an electrical signal when stimulated, commercially available from a multiple vendors, and a resistive film type force sensor capable of generating an electrical signal when stimulated, for example, Flexi-Force Sensor® commercially available from Tekscan Inc.

Figure 7B:
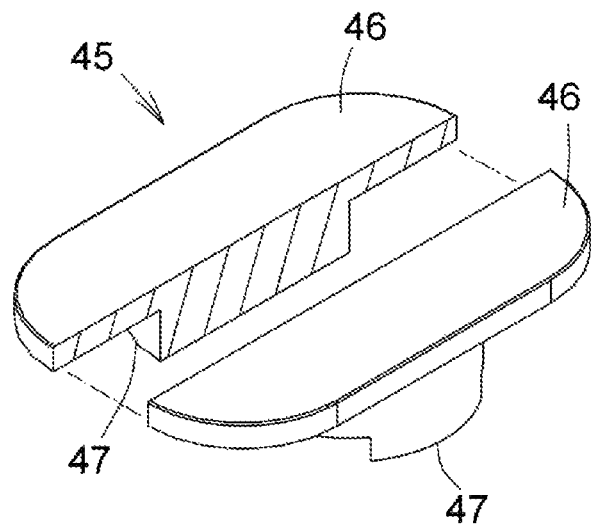
FIG. 7B is a perspective view of a compression head comprising a force gauge assembly sectioned along a long symmetry plane and spaced apart according to an alternate embodiment of the present invention.
Figure 7C:
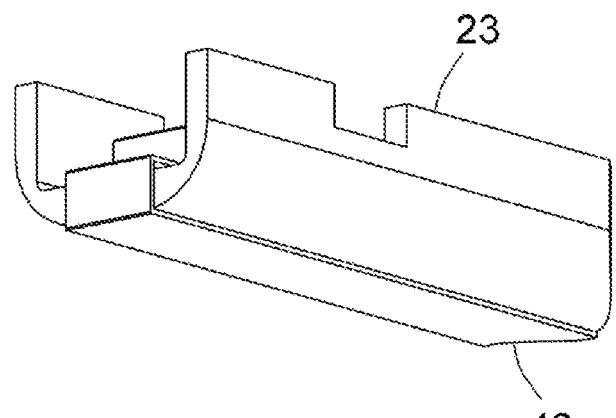
FIG. 7C is a perspective view of a signal conduction means and a cartridge jaw member partially broken away according to an embodiment of the present invention.
Figure 7D:
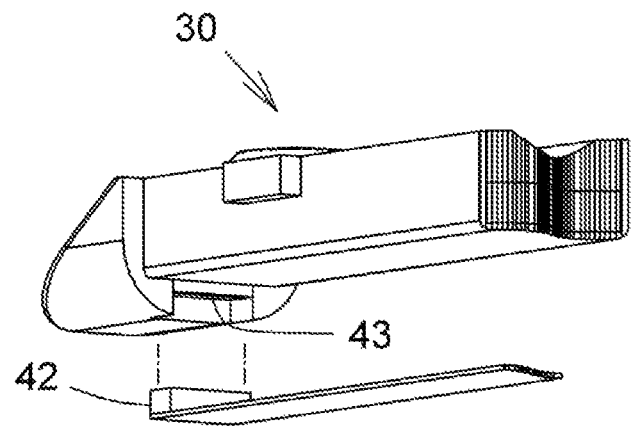
FIG. 7D is a perspective view of a signal conduction means comprising a compression gauge cartridge partially broken away according to an alternate embodiment of the present invention.

Preferably, signal conduction means 48, appropriately selected for force transducer 41, may work bi-directionally conducting a signal from force transducer 41 to a force transducer indicator or a controller disposed remotely from a surgical site for signal processing and display of result therefrom and providing a power and control signals needed for operation of force transducer. As shown in FIG. 7C, signal conduction means 48 may be routed to pass around a distal end of cartridge jaw member 23 as it exits cartridge body 31 in an embodiment of the present invention. As shown in FIG. 7D, in an alternate embodiment, signal conduction means 48 may be configured to comprise at least two parts, one part connected to force transducer 41 on one end and terminating with a connector 43 on the other end, and the other part connected to a force transducer indicator on one end and terminating to a connector 42 complementary to connector 43 on the other end. In an embodiment a force transducer indicator or a controller may be disposed externally to the patient and may include an off-the-shelf, commercial weight indicator unit, a custom designed, microprocessor controlled indicator and a signal processor electronics controlled by a computer with a display. In an alternate embodiment of the present invention, at least for a force transducer configured to be electrically powered and generate an electric signal when stimulated, an electrical power source, for example, a battery, and at least a part of processing and display circuitry may be disposed in and supported by a cartridge body comprising a compression gauge cartridge. In another alternate embodiment the cartridge body may further include a wireless communication means for wirelessly sending a signal to an indicator or a controller disposed externally from a surgical site for further processing and display.

In an embodiment, force transducer 41 may be dimensionally adaptable for use supported in a cartridge body disposed in a cartridge bay of a cartridge jaw member of an end effector. In an alternate embodiment, force transducer 41 may be dimensionally adaptable for use supported in one of the jaw members comprising an end effector of a surgical instrument dedicated to implementation of the present invention. Preferably, the deflection of a deflectable portion of force transducer 41, which normally accompanies operation of force transducer 41 in varying forms and to a different degree, at a maximum level of the reactionary load from the compressed tissue does not exceed a predetermined fraction of a strain induced on the tissue by the compression applied thereto. As previously described in reference to FIG. 1, a relatively small change in the strain of a tissue, for example, due to interaction with force transducer 41, could result in a substantial variation in the stress thereof potentially skewing the measurement of the reactionary load therefrom. Typically, a maximum deflection a strain gauge based load cell or a hydraulic load cell experiences at the load limit does not exceed a few thousandths of an inch easily satisfying the requirement for use on a tissue. A load cell of a planar configuration, at least those include in the examples described previously, does not require any deflection to perform a force measurement.

In an embodiment of the present invention, compression head 45 comprising force gauge assembly 40 mechanically interfaces between a tissue undergoing compression and force transducer 41 for measuring a reactionary force therefrom. Referring to FIGS. 3A-5B and 7A, 8A and 9A, in an embodiment compression head 45 may be configured and disposed, with respect to cartridge body 31, to contact force transducer 41 on one end, a transducer contact face 47, and the tissue on the other end, tissue compression face 46 participating in compression of the tissue cooperating with anvil jaw member 21 and transferring a reactionary load from the compressed tissue to force transducer 41 substantially without a mechanical loss in a manner conducive to the mode of operation of a particular force transducer. In an embodiment compression head 45 may be configured and disposed, with respect to cartridge body 31, so that tissue compression face 46 thereof lies substantially closer to tissue contacting surface 24 of anvil jaw member 21 than tissue supporting surface 34 of cartridge body 31 as schematically shown in FIG. 6D showing, in a side elevation view, a tissue compressed between compression gauge cartridge 30 and anvil jaw member 21 comprising an end effector in a closed position. This is to deliberately encourage the compression of a tissue to take place preferentially over an area, out of tissue contacting surface 24 of an anvil jaw member 21, covered by tissue compression face 46 and to minimize tissue compression over tissue supporting surface 34 to a predetermined gap distance between tissue compression face 46 and tissue contacting surface 24 indicated by a letter G in FIG. 6D.

Figure 8B:
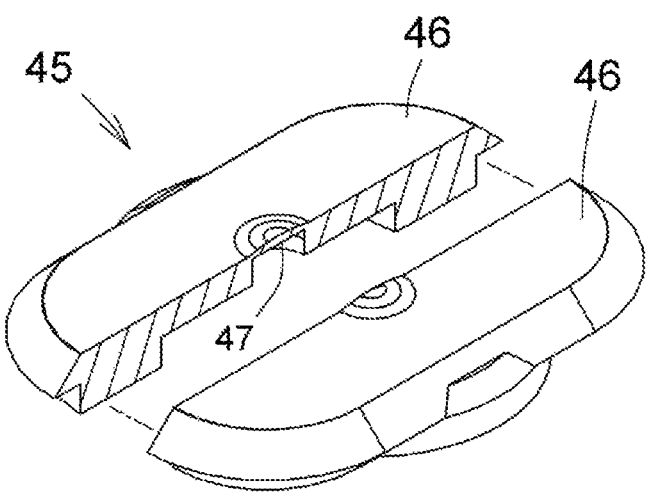
FIG. 8B is a perspective view of a compression head comprising a force gauge assembly sectioned along a long symmetry plane and spaced apart according to another alternate embodiment of the present invention.
Figure 8C:
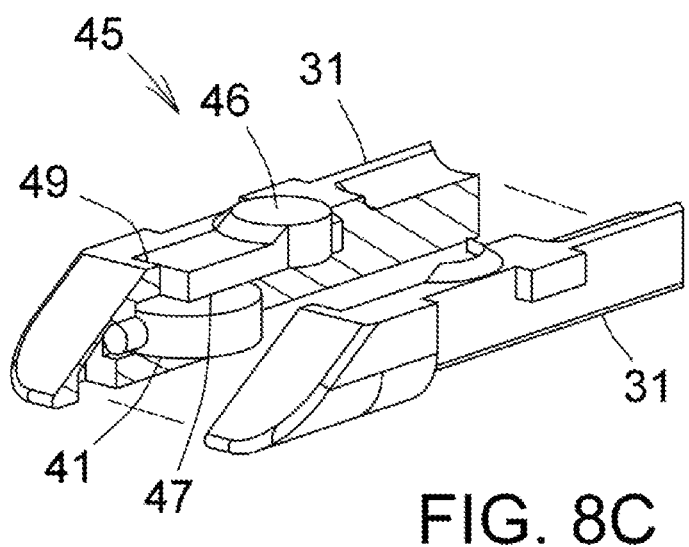
FIG. 8C is a perspective view of a cantilevered compression head comprising a force gauge assembly disposed in a cartridge body shown partially broken away, sectioned along a symmetry plane and spaced apart according to another alternate embodiment of the present invention.
Figure 8D:
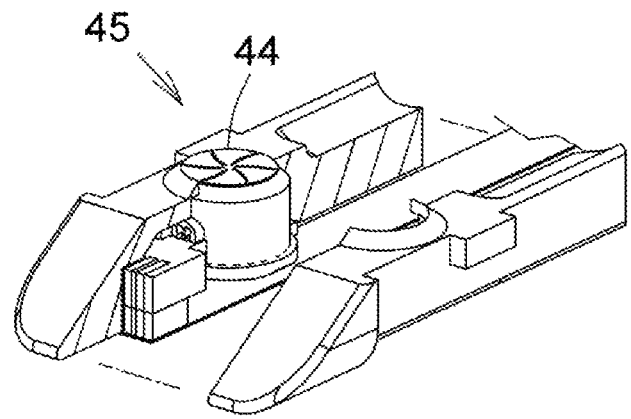
FIG. 8D is a perspective view of a deformable compression head comprising a force gauge assembly disposed in a cartridge body shown partially broken away, sectioned along a symmetry plane and spaced apart according to an another alternate embodiment of the present invention.
Figure 9B:
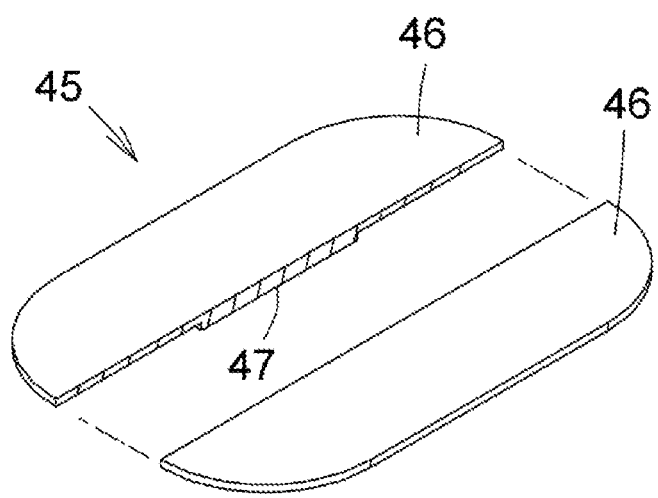
FIG. 9B is a perspective view of a compression head comprising a force gauge assembly sectioned along a symmetry plane and spaced apart according to an another alternate embodiment of the present invention.

In various embodiments of the present invention compression head 45 may take on different configurations and mechanical characteristics that suit a particular application of a compression gauge cartridge of the present invention. For example, as shown in FIGS. 7B, 8B and 9B, configuration of transducer contact face 47 may be varied to accommodate force transducer 41 of different geometry, and the area and profile of tissue compression face 46 may be predetermined, for example, to control the degree of tissue compression optionally in conjunction with variation of a gap distance between tissue compression face 46 and tissue contacting surface 24, which is primarily controllable with a spacer member 50, as will be described hereinafter. In an embodiment compression head 45 may be of substantially rigid construction to be able to transfer a reactionary load imparted on tissue compression face 46 thereof to transducer contact face 47 without a mechanical loss even when the reactionary load is unevenly distributed over tissue compression face 46. In an alternate embodiment compression head 45 may be of substantially rigid construction to be able to resist deformation under a compressive load imparted thereon by the compressed tissue but otherwise of flexible nature as may be the case for a relatively thin compression head that may be employed for a force transducer of a planar configuration as schematically illustrated in FIG. 9B. In an embodiment of the present invention compression head 45 may be configured to float, that is, be left unattached other than the mechanical engagement with force transducer 41 through transducer contact face 47 thereof. In an alternate embodiment compression head 45 may be fixedly joined with cartridge body 31 in such a configuration that allows a displacement thereof, and concomitant deflection of force transducer 41, in response to a reactionary load from a compressed tissue to occur through a predetermined deformation of compression head 45. In an exemplary embodiment, as previously described with reference to FIGS. 3C and 3D, compression head 45 may be fixedly joined with seal member 37 having sufficient flexibility to provide freedom of movement thereto. In an alternate exemplary embodiment, as shown in FIG. 8C, compression head 45 may be configured and disposed to cantilever with respect to a fixed position 49 on cartridge body 31 with tissue compression face 46 thereof positioned remotely from fixed position 49 and transducer contact face 47 positioned therebetween. In another alternate exemplary embodiment, compression head 45 may comprise a deformable member 44 fixedly joined with cartridge body 31 in a predetermined pattern, for example, along the periphery as shown in FIG. 8D schematically illustrating a cartridge body sectioned and spaced apart, and a force gauge assembly, that is configured to flex substantially perpendicularly, i.e., up and down, with respect to tissue contacting surface 46 of cartridge body 31.

Figure 10A:
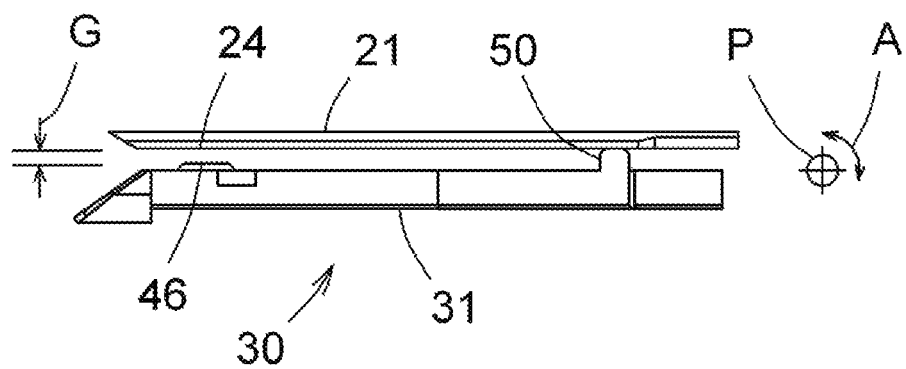
FIGS. 10A and 10B are side elevation views of a compression gauge cartridge comprising a cartridge jaw member and an anvil jaw member according to embodiments of the present invention.
Figure 10B:
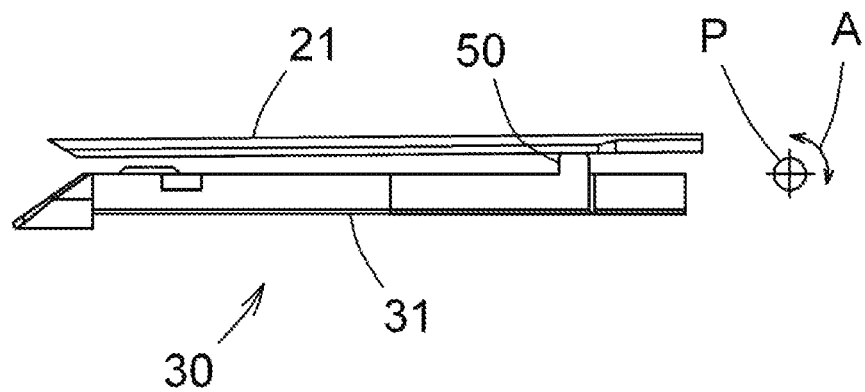

Referring to FIGS. 3A-5B, in a preferred embodiment of the present invention spacer member 50 may be of a rigid construction extending from tissue supporting surface 34 of cartridge body 31 disposed between proximal end 33 and distal end 32 thereof and proximal to compression head 45 comprising force gauge assembly 40. In an embodiment spacer member 50 may be configured to be a positive stop constraining a pivotal motion of the two jaw members comprising an end effector and substantially defining the closest gap distance at the position of spacer member 50 between tissue contacting surfaces 24, 26 of anvil jaw member 21 and cartridge jaw member 22. In the absence of a deflection of an anvil jaw member, spacer member 50 also determines a predetermined gap distance between tissue compression face 46 of compression head 45 and tissue contacting surface 24 of anvil jaw member 21 with two jaw members comprising an end effector in a fully closed position. Spacer member 50 also plays an important role in substantially eliminating variation in the gap distance stemming from a play present in the pivot and drive mechanisms of a pivotal joint of the two jaw members comprising an end effector. Referring to FIGS. 10A and 10B schematically showing, in a side elevation view, a positional relationship between a cartridge jaw member represented by compression gauge cartridge 30 and an anvil jaw member in a fully closed position, in an embodiment of the present invention, spacer member 50 may be dimensioned to make the two planes, substantially defined by tissue supporting surface 34 and tissue contacting surface 24, respectively, to be substantially parallel with each other in providing a predetermined gap distance G between tissue compression face 46 and tissue contacting surface 24. In an alternate embodiment spacer member 50 may be dimensioned to make the two planes to be at a predetermined angle with each other in providing a predetermined gap distance G between tissue compression face 46 and tissue contacting surface 24. In a further embodiment spacer member 50 may be dimensioned so that substantially all the plays in a pivot mechanism and a drive mechanism of a pivotal joint of the two jaw members are fully taken up when the two jaw members are in fully closed position as will be further described in the following section.

Figure 11A:
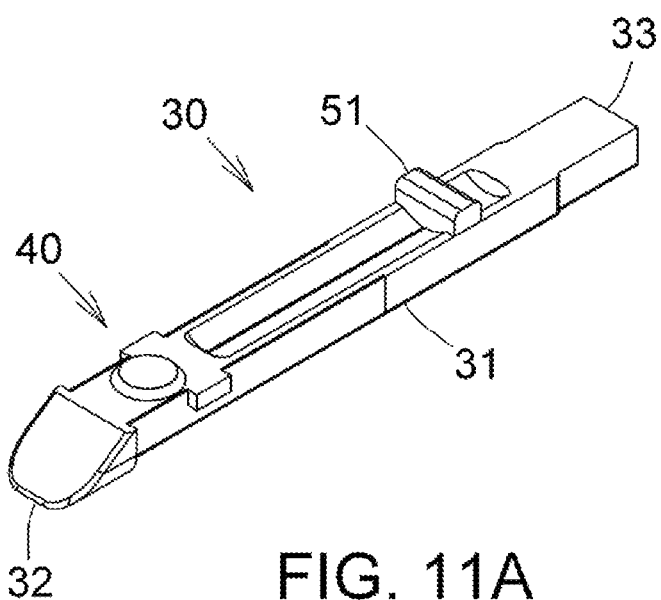
FIG. 11A is a perspective view of a cartridge body and a repositionable spacer member comprising a compression gauge cartridge according to an embodiment of the present invention.

In a preferred embodiment of the present invention, spacer member 50 comprising compression gauge cartridge 30 may be a block of a rigid construction fixedly joined with cartridge body 31. As shown in FIG. 11A, in an embodiment cartridge body 31 and spacer member 51 may be configured so that the position of spacer member 51 along the length of cartridge body 31 may be changed to suit a particular application of a compression gauge cartridge of the present invention. Spacer member 50 plays a significant role in substantially eliminating variation in the positional relationship between the two jaw members comprising an end effector due to plays present in the pivot and drive mechanisms of a pivotal joint of the two jaw members by acting as a rigid fulcrum disposed between the pivot mechanism and a compression head comprising a force gauge assembly that forces the plays to be fully taken up when the two jaw members reach a fully closed and, in some cases, locked position. Even when the tissue contacting surface of the anvil jaw member comes to rest making contact with the spacer member as the two jaw members close driven by the drive mechanism, the drive mechanism continues to drive the pivot mechanism to rotate one or both of the jaw members with respect to the point of contact between the anvil jaw member and the spacer member until all the plays in the pivot and drive mechanisms are fully taken up and the pivotal motion of the two jaw members comes to a solid stop reaching a final positional relationship there-between. Since, in practice, the force involved in driving the pivotal motion of the two jaw members are, by design, much larger than the largest reactionary load normally expected from a compressed tissue between the two jaw members comprising an end effector of a surgical stapler instrument, the final positional relationship between the two jaw members thus achieved remains substantially undisturbed even when the two jaw members are acted upon from the reactionary load from a compressed tissue there-between and is solely determined by the position and configuration of spacer member 50. Barring potential deflection of the anvil jaw member under a reactionary load from a compressed tissue, which can be effectively kept under control as previously described, spacer member 50 thus enables a surgical stapler instrument implemented with a compression gauge cartridge of the present invention to be used, without modification, to provide a predetermined gap distance, between the compression face of the compression head and the tissue contacting surface of the anvil jaw member, consistently and with high degree of repeatability, and concomitantly to compress a tissue consistently to a thickness corresponding to the predetermined gap distance.

Figure 11B:
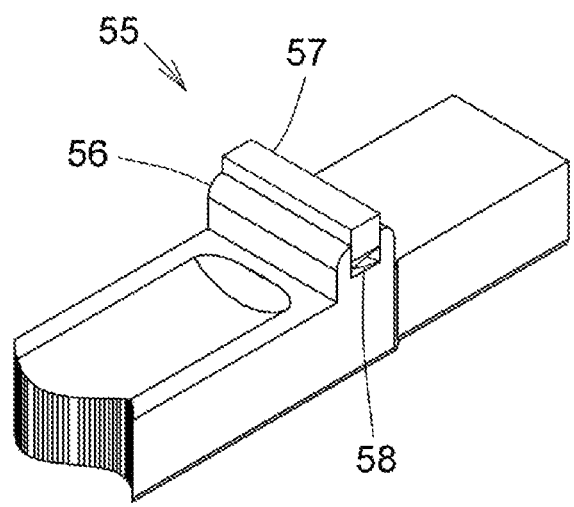
FIGS. 11B and 11C are perspective views of a spacer member with an extension member according to embodiments of the present invention.
Figure 11C:
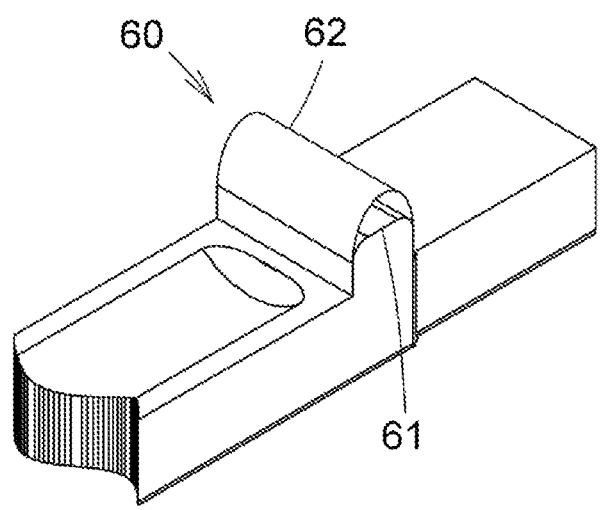
Figure 11D:
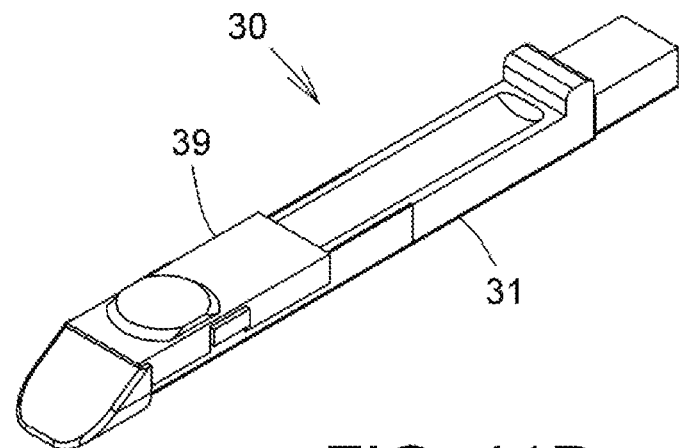
FIG. 11D is a perspective view of a protective cover disposed on a cartridge body comprising a compression gauge cartridge according to an embodiment of the present invention.

In an embodiment of the present invention, a spacer member also functions as a tissue stop defining a proximal most position along the cartridge body to which a tissue can be introduced between the two jaw members comprising an end effector. Referring to FIGS. 11B and 11C, in an embodiment spacer member 55, 60 may further comprise a spacer extension member 57, 62 for preventing a portion of a tissue getting caught, while being captured, and subsequently pinched between a spacer member and a tissue contacting surface of an anvil jaw member as the two jaw members are closed. As shown in FIG. 11B, in an embodiment spacer extension member 57 may be of a retractable/extendable type configured to move in and out of a spacer member body 56, for example, a spring 58 loaded plunger or detent biased to extend out of a cavity in spacer member body 56 to a preset limit and to follow the pivotal motion of the two jaw members keeping the gap between the spacer member and the tissue contacting surface of an anvil jaw member closed. In an alternate embodiment, as shown in FIG. 11C, spacer extension member 62 may be of a collapsible/expandable type including an air filled bladder, resilient foam, a metal spring element and a leaf spring element made of a stiff polymer film, etc, configured to require a minimal force to be collapsed down to a spacer member body 61. Referring to FIG. 11D, in an embodiment a compression gauge cartridge may comprise a protective cover 39 providing protection, for example, undesirable impact during handling, over at least part of cartridge body 31 thereof, preferably, including the general area around the position of the force gauge assembly.

Figure 12A:
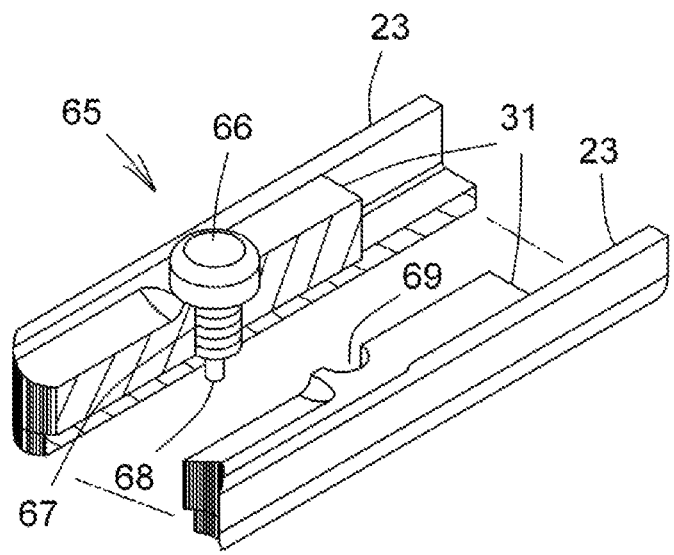
FIGS. 12A-12C are perspective views of a cartridge body and a cartridge bay, partially broken away and sectioned and spaced apart, and an adjustable spacer member comprising a compression gauge cartridge according to various embodiments of the present invention.
Figure 12B:
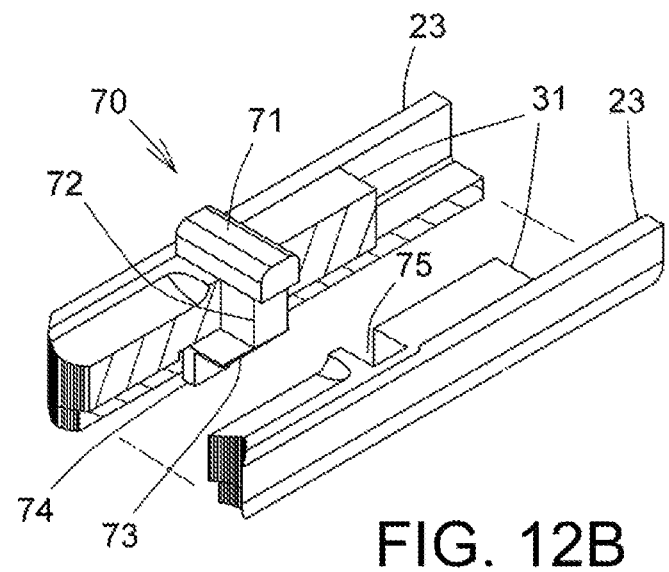
Figure 12C:
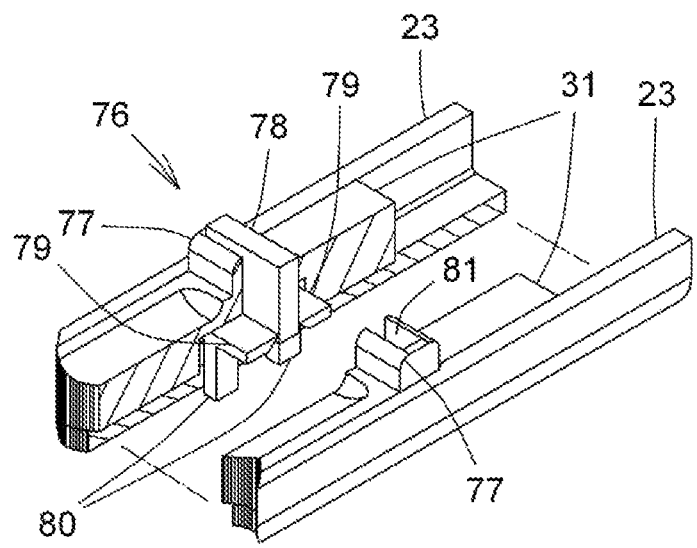

Referring to FIGS. 12A-12C showing a spacer member, and a cartridge body 31 and a cartridge bay 23 broken away and sectioned apart, in an embodiment of the present invention, a spacer member comprising a compression gauge cartridge may be configured so that the height thereof over the tissue supporting surface of the cartridge body, i.e., the vertical extent the spacer member extends from the tissue supporting surface, may be adjusted. As shown in FIG. 12A, in an embodiment of the present invention, an adjustable spacer member 65 having an anvil contacting face 66 may be mounted on a threaded base 67 of a gender disposed in a hole 69 in cartridge body 31 with a matching thread of an opposite gender so that the vertical position of anvil contacting face 66 may be adjusted by turning a control stem 68 fixedly joined with threaded base 67 and disposed through a slot normally found in cartridge bay 23. As shown in FIG. 12B, in an alternate embodiment, an adjustable spacer member 70 having an anvil contacting face 71 may comprise a rigid base 72 disposed in a hole 75 in cartridge body 31 and on a wedge shape platform 73 joined with a control stem 74 disposed through a slot in cartridge bay 23 so that the vertical position of anvil contacting face 71 may be adjusted and locked in a position by sliding control stem 74 along the slot. As shown in FIG. 12C, in another alternate embodiment, an adjustable spacer member 76 may be configured to have a nested structure comprising a stationary base 77 and a movable plunger 78 slidably engaged with stationary base 77 in a hole 8 1for vertical movement with respect to the tissue supporting surface and to include at least one break member 79 with a predetermined breaking mechanism, for example, a sharp edge, drivable with control stems 80 fixedly joined therewith and disposed through a slot in cartridge bay 23 so that movable plunger 78 may be securely held immobile once the desired vertical position thereof is reached. In an embodiment adjustable spacer member 65, 70, 76 may be configured with a bias spring that drives adjustable spacer member or a movable part thereof to a final position when triggered by a predetermined event, an example of which will be described hereinafter.

Figure 12D:
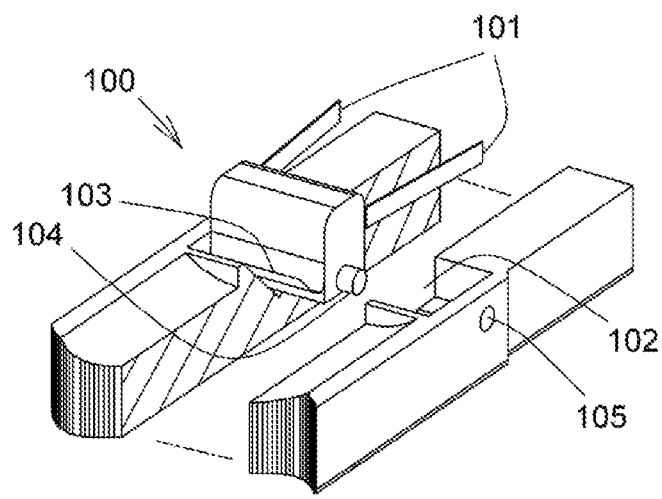
FIGS. 12D and 12E are perspective views of a cartridge body and a cartridge bay, partially broken away and sectioned and spaced apart, and a rotatable spacer member comprising a compression gauge cartridge according to an alternate embodiment of the present invention.
Figure 12E:
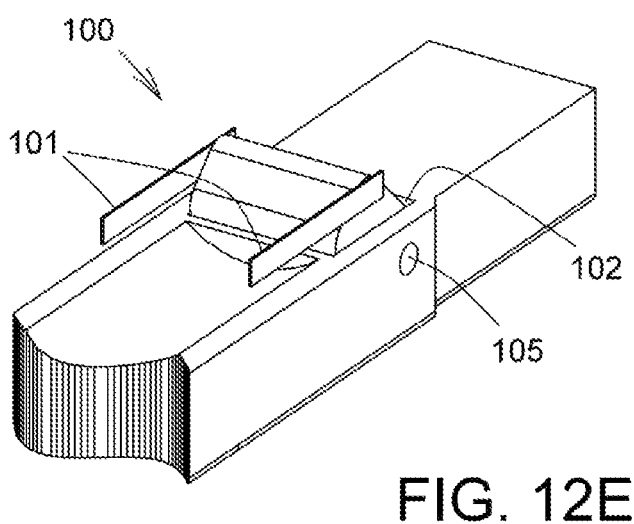

As shown in FIGS. 12D and 12E, in an embodiment of the present invention a spacer member 100 may be configured to include an axle 104, a spring element 103 and at least one flap member 101, and to be disposed in a cavity 102 in a cartridge body comprising a compression gauge cartridge with axel 104 rotatably mated with a pair of holes 105 in the cartridge body so that spacer member 100 may pivot with respect to the cartridge body around axle 104. Spring element 103 may be configured to bias spacer member 100 so that it remains up right with respect to the cartridge body ready to withstand the downward load from the anvil member when the two jaw members comprising the end effector are in a fully closed position. At least one flap member 101 may be configured and disposed with respect to spacer member 100 so that it may be flipped proximally and distally therewith when acted on by the proximal and distal ends of a trocar, respectively, during insertion and removal there-through of a surgical stapler instrument instrumented with the compression gauge cartridge. In an embodiment spacer member 100 may be rotated to reduce the height thereof above the cartridge body, as schematically shown in FIG. 12E, manually by a physician prior to insertion of a surgical stapler instrument or automatically by the interaction thereof with the distal end of the trocar during removal of a surgical stapler instrument. A spacer member of such a configuration would enable use of a compression gauge cartridge with a spacer member so tall that would make an end effector of a surgical stapler instrument instrumented with a compression gauge cartridge impassable through a normally used trocar even with the jaw members in a fully closed position.

Figure 13A:
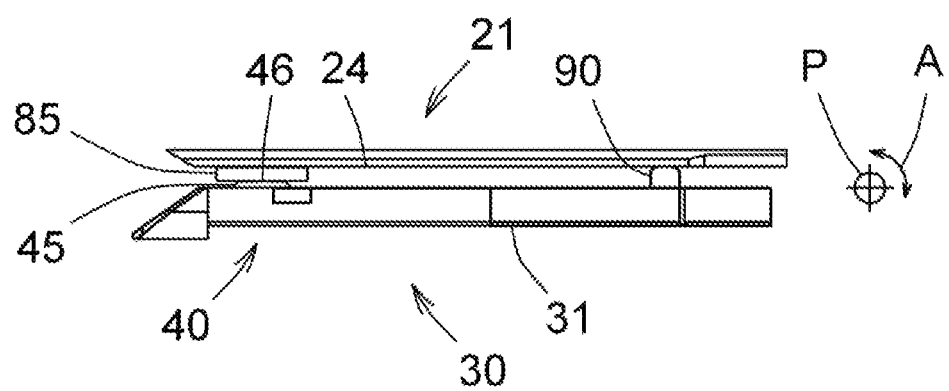
FIG. 13A is a schematic, side elevation view of a reference block, a compression gauge cartridge and an anvil jaw member according to an embodiment of the present invention.
Figure 13B:
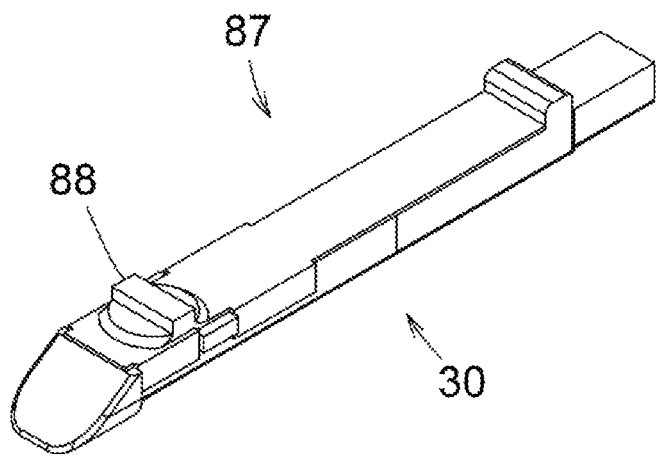
FIG. 13B is a perspective view of a protective cover disposed on a cartridge body according to an embodiment of the present invention.
Figure 13C:
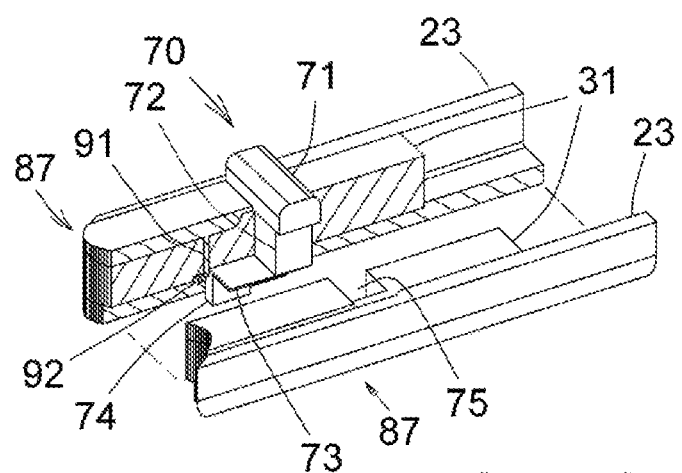
FIG. 13C is a perspective view of a cartridge body, a protective cover and a cartridge bay, partially broken away and sectioned and spaced apart, and an adjustable spacer member biased by a spring according to an embodiment of the present invention.

Surgical stapler instrument products of a design, like any other engineering products, inherently includes certain variations in their mechanical performance, which, by design, are not of significance in originally intended uses in surgical stapling operation but may negatively affect uses of a surgical stapler instrument instrumented with a compression gauge cartridge of the present invention. For example, such variations could manifest between different production lots, for example, due to change in production steps and/or even between different instruments from the same production lot, for example, due to changes in the manufacturing tolerances of parts and/or subassemblies. As described previously, changes in the plays in the pivot and drive mechanism of a surgical stapler instrument, for example, resulting from variations in manufacturing tolerances may degrade the precision in the final positional relationship between the two jaw members in a fully closed and locked position and, in turn, the predetermined gap distance between the tissue compression face of the compression head and the tissue contacting surface of the anvil jaw member corresponding to a predetermined thickness to which a tissue is compressed. To circumvent the potential impact these variations may have on the performance of a compression gauge cartridge mounted on a surgical stapler instrument or in a surgical compression gauge instrument, in various embodiments of the present invention, there are provided methods for calibrating the gap distance between the tissue compression face of the compression head and the tissue contacting surface of the anvil jaw member. Referring to FIG. 13A showing, in a side elevation view, an anvil jaw member 21 and a compression gauge cartridge 30 representing a cartridge jaw member, in an embodiment a gap distance calibration method comprises steps of: (1) positioning a reference block 85 over a compression head 45 of height corresponding to a predetermined gap distance between tissue compression face 46 of compression head 45 and the tissue contacting surface 24 of anvil jaw member 21; (2) fully closing the two jaw members of the end effector; and (3) adjusting the height of an adjustable spacer member 90 until the load cell indicator reads zero. In an embodiment the height of reference block 85 may be fine tuned to reflect possible deflection of anvil jaw member 21 due to a reactionary load from reference block 85 during the gap distance calibration procedure. For example, reference block 85 may be made taller than a predetermined target gap distance to account for deflection of anvil jaw member 21. In an embodiment fully closing the two jaw members may involve operating a handle assembly comprising a surgical stapler instrument or a surgical compression gauge instrument to close the two jaw members until the handle assembly reaches a locked state corresponding to a limit of the closing operation. In an alternate embodiment a gap distance calibration method comprises steps of: (1) positioning reference block 85 over a compression head 45 of height corresponding to a predetermined gap distance between tissue compression face 46 of compression head 45 and tissue contacting surface 24 of anvil jaw member 21; (2) fully closing the two jaw members of the end effector; and (3) adjusting the height of adjustable spacer member 90 until it touches tissue contacting surface 24 of anvil jaw member 21. In another alternate embodiment a gap distance calibration method comprises steps of: (1) positioning a reference material over a compression head 45 of known tensile property and dimension between tissue compression face 46 of compression head 45 and tissue contacting surface 24 of anvil jaw member 21; (2) fully closing the two jaw members of the end effector; and (3) adjusting the height of adjustable spacer member 90 until the load cell indicator reads a predetermined value indicating the reference material is compressed to a thickness corresponding to a predetermined gap distance between tissue compression face 46 of compression head 45 and tissue contacting surface 24 of anvil jaw member 21. As shown in FIGS. 13B and 13C, in an embodiment of the present invention a protective cover 87 may be configured to comprise a built-in reference block 88 and a trigger member 91 for causing a spring 92 to drive a locking mechanism 73, 74 for adjustable spacer member 70 to facilitate the gap calibration procedure.

Figure 14:
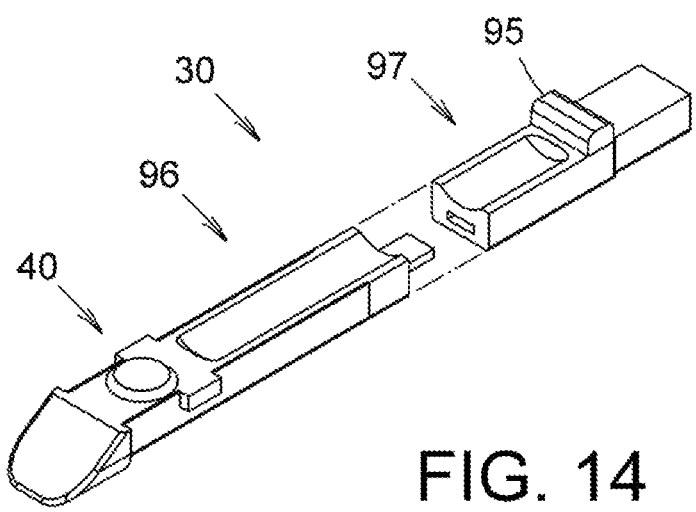
FIG. 14 is an assembly view of a compression gauge cartridge comprising two parts according to an alternate embodiment of the present invention.

Referring to FIG. 14, in an embodiment of the present invention, a compression gauge cartridge 30 may comprise two parts 96, 97, preferably, one part 96 including a force gauge assembly 40 and the other part 97 including a spacer member 95, that are configured to be releasably joined with each other. In an embodiment part 96 may be a part of compression gauge cartridge 30 that can be effectively re-sterilized and part 97 difficult to re-sterilize, for example, due to internal structures present if spacer member 95 is an adjustable spacer member as previously described. After use, part 96 may be kept for reuse following a re-sterilization and used part 97 may be discarded and exchanged with a new one.

Figure 15:
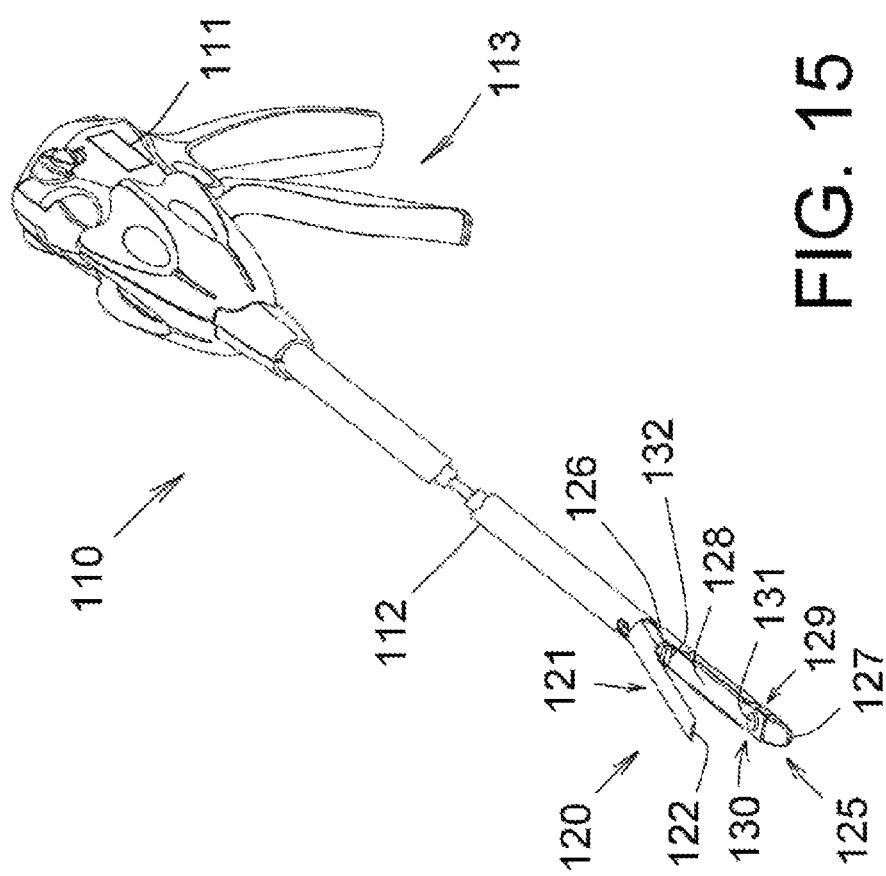
FIG. 15 is a perspective view of a surgical compression gauge instrument comprising a compression gauge jaw member according to an embodiment of the present invention.

Referring to FIG. 15, in an embodiment of the present invention, a surgical compression gauge instrument 110 for compressing a tissue consistently to a predetermined thickness and measure a reactionary load therefrom for assisting selection of a staple cartridge and assessing a condition of a tissue comprises: a handle portion 111; a body portion 112 extending distally from handle portion 111 and defining a longitudinal axis; and a tool assembly 120 at a distal end of and operatively connected to body portion 112, tool assembly 120 comprising an anvil jaw member 121 having a tissue contacting surface 122 and a compression gauge jaw member 125, configured to open and close when operated by handle portion 111, wherein compression gauge jaw member 125 having a proximal end 126 and a distal end 127, and a tissue supporting surface 128 comprises a force gauge assembly 129 comprising a force transducer (not shown in the FIGURE) and a compression head 130 having a tissue compression face 131, supported by compression gauge jaw member 125 positioned between proximal end 126 and distal end 127 thereof, and wherein compression head 130 of force gauge assembly 129 is disposed so that tissue compression face 131 thereof lies substantially closer to tissue contacting surface 122 of anvil jaw member 121 than tissue supporting surface 128 of compression gauge jaw member 125; and a spacer member 132 extending from tissue supporting surface 128 comprising compression gauge jaw member 125, wherein force gauge assembly 129 is positioned distally with respect to spacer member 132.

In a preferred embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from the standard set of staple cartridges containing staples of a height corresponding to said predetermined thickness of said compressed tissue if the result of comparison is case (1), or a staple cartridge containing staples of a height smaller than said predetermined thickness of said compressed tissue taking into account said size of difference if the result of comparison is case (2), or a staple cartridge containing staples of a height larger than said predetermined thickness of said compressed tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined average height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to an average height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from said standard set of staple cartridges containing staples of an average height corresponding to said predetermined thickness of said compressed tissue if the result of comparison is case (1), or a staple cartridge containing staples of an average height smaller than said predetermined thickness of said compressed tissue taking into account said size of difference if the result of comparison is case (2), or a staple cartridge containing staples of an average height larger than said predetermined thickness of said compressed tissue taking into account said size of difference if the result of comparison is case (3). In an alternate embodiment, a method for selecting a staple cartridge from the standard set of staple cartridges, each containing staples of a predetermined average height, optimal for a tissue of a surgical stapling operation may further comprise a step of waiting for a predetermined length of time after closing said cartridge jaw member and said anvil jaw member to compress said tissue.

In another alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a green cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value; selecting a green cartridge from the standard set of staple cartridges if the result of comparison is case (1) or a blue cartridge if the result of comparison is case (2), or a black cartridge if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; providing a reference tissue for which an optimal staple height for a surgical stapling operation is known; comparing said reactionary load reading with a reactionary load from said reference tissue compressed to said predetermined thickness over the same area of said reference tissue as that of said tissue compression face of said compression head to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

Figure 16:
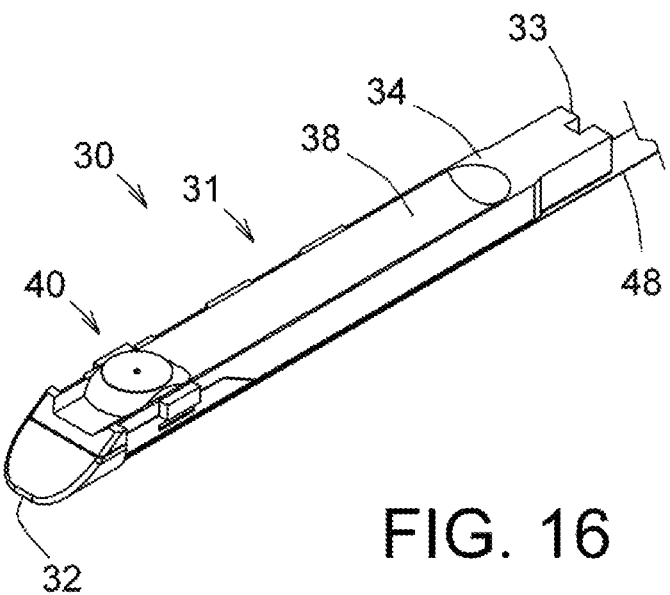
FIG. 16 is a perspective view of a compression gauge cartridge according to an alternate embodiment of the present invention.
Figure 17:
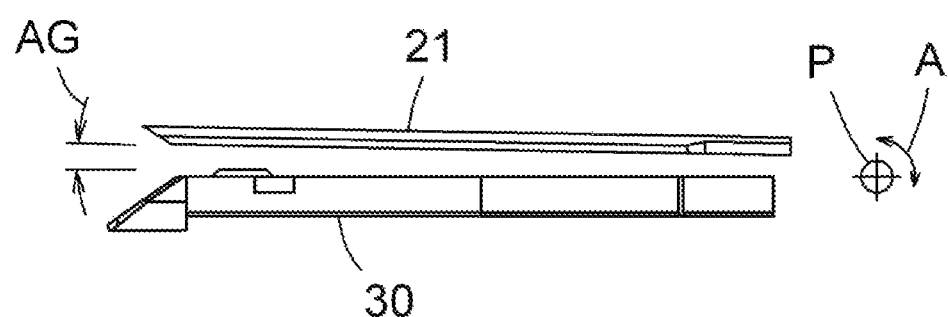
FIG. 17 is a side elevation view of a compression gauge cartridge comprising a cartridge jaw member and an anvil jaw member according to embodiments of the present invention.
Figure 19:
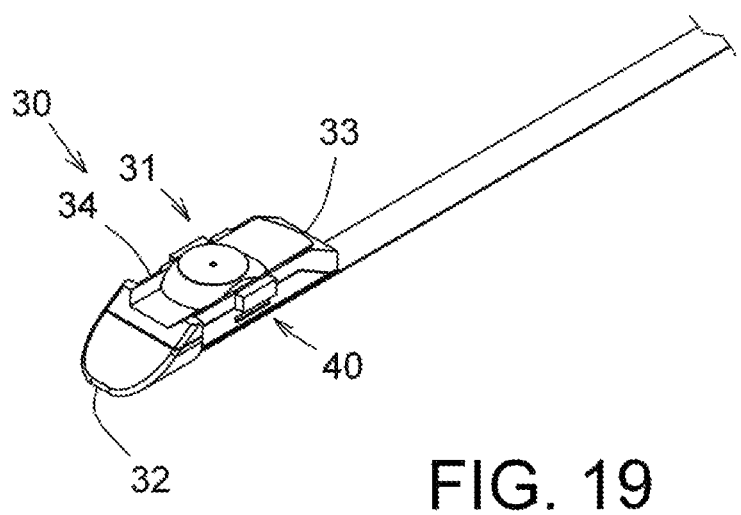
FIG. 19 is a perspective view of a compression gauge cartridge according to an alternate embodiment of the present invention.

Referring to FIG. 16, showing a compression gauge cartridge 30 in a perspective view in an embodiment of the present invention, compression gauge cartridge 30 for use mounted in a cartridge bay of a cartridge jaw member comprising an end effector of a surgical stapler instrument, together with an anvil jaw member having a tissue contacting surface, to compress a tissue so that said cartridge jaw member and said anvil jaw member come to a predetermined angular positional relationship with each other, as indicated in FIG. 17 by a label AG in a schematic representation of an anvil jaw member 21 and compression gauge cartridge 30, and measure a reactionary load therefrom for assisting in selection of a staple cartridge optimal for a tissue of a surgical stapling operation comprises: a cartridge body 31 having a proximal end 32 and a distal end 33, and a tissue supporting surface 34, wherein cartridge body 31 may be configured for compression gauge cartridge 30 to be releasably mounted in said cartridge bay and for tissue supporting surface 34 to be at least at a predetermined distance from said tissue contacting surface of said anvil jaw member when cartridge jaw member and said anvil jaw member are in a fully closed position; and a force gauge assembly 40 comprising a force transducer and a compression head having a tissue compression face, wherein force gauge assembly 40 may be supported by cartridge body 31 positioned between proximal end 32 and distal end 33 thereof, and wherein said compression head comprising said force gauge assembly 40 may be configured and disposed so that said tissue compression face thereof may lie substantially closer to said tissue contacting surface of said anvil jaw member than tissue supporting surface 34 of cartridge body 31. In an alternate embodiment tissue supporting surface 34 of cartridge body 31 may be contoured in such a way to further reduce compression of a tissue disposed between tissue supporting surface 34 and said tissue contacting surface when said cartridge jaw member and said anvil jaw member are in a fully closed position. Compression gauge cartridge 30 is configured to allow an existing surgical stapler instrument to be used without modification in applying a compression to a predetermined area of a tissue captured between the two jaw members comprising an end effector thereof so that the two jaw members come to a predetermined positional relationship with each other and measuring a reactionary load from the compressed area of the tissue. In an embodiment of the present invention cartridge body 31 comprising compression gauge cartridge 30 may be configured for compression gauge cartridge 30 to be releasably mounted and securely retained in a cartridge bay comprising a cartridge jaw member of an end effector. In an alternate embodiment cartridge body 31 comprising compression gauge cartridge 30 may be configured to be fixedly mounted in a cartridge bay to be integrated with a cartridge jaw member of an end effector of a surgical stapler instrument. In another alternate embodiment cartridge body 31 comprising compression gauge cartridge 30 may be configured to be fixedly mounted in a cartridge bay to be integrated with a cartridge jaw member of an end effector comprising a disposable reload unit of a certain surgical stapler instrument product in the market. In an alternate embodiment of the present invention the dimension of a cartridge body comprising a compression gauge cartridge may be varied to suit particular application thereof. For example, as shown in FIG. 19, cartridge body 31 may be configured to be shorter than a conventional staple cartridge along the length of a cartridge bay.

Figure 18:
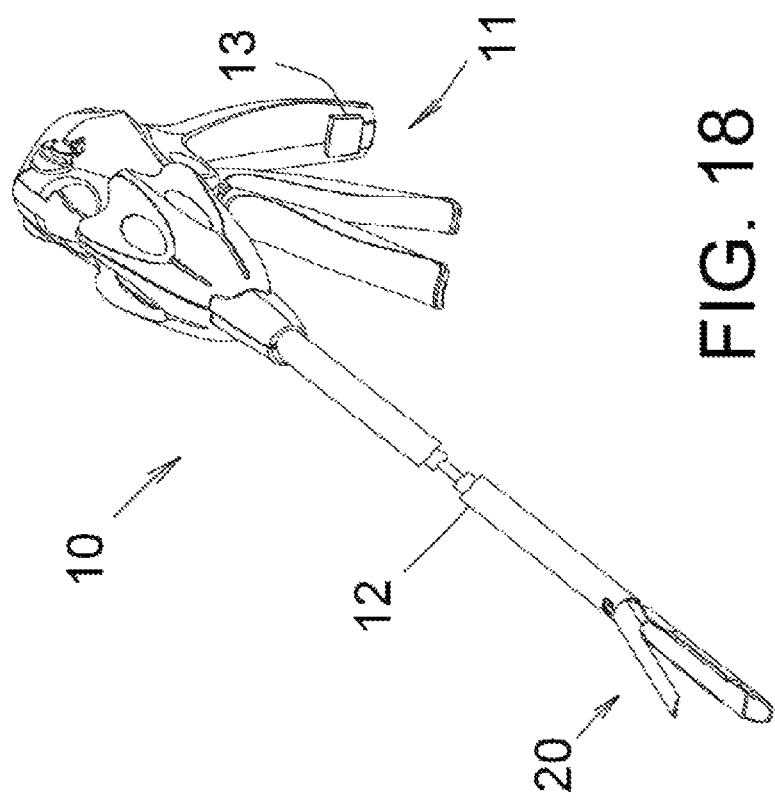
FIG. 18 is a perspective view of a surgical stapler instrument according to an embodiment of the present invention.

Referring to FIG. 18, in an embodiment of the present invention, a surgical stapler instrument 10 may further include a spacer block 13 of a predetermined height disposed at a handle 11 comprising surgical stapler instrument 10 for defining a predetermined extent handle 11 may be operated to close a cartridge jaw member and an anvil jaw member comprising an end effector 20 comprising surgical stapler instrument 10 so that said cartridge jaw member and said anvil jaw member come to a predetermined angular positional relationship with each other.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member having a tissue contacting surface, of a surgical stapler instrument; capturing a tissue between said cartridge jaw member and said anvil jaw member; closing said cartridge jaw member and said anvil jaw member to compress said tissue captured there-between so that said cartridge jaw member and said anvil jaw member come to a predetermined angular positional relationship with each other; reading out a reactionary load from said compressed tissue displayed on a force transducer indicator; providing a reference tissue for which an optimal staple height for a surgical stapling operation is known; comparing said reactionary load reading with a reactionary load from said reference tissue compressed so that said cartridge jaw member and said anvil jaw member come to said predetermined angular positional relationship with each other to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

Figure 20:
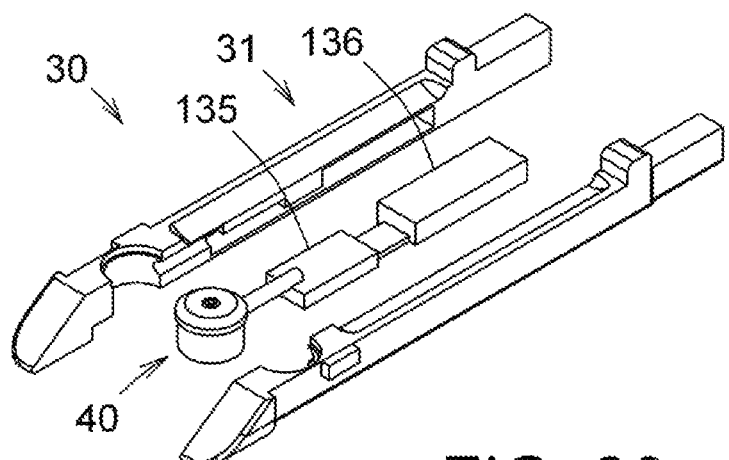
FIG. 20 is a perspective view of a compression gauge cartridge with a cartridge body sectioned similarly to that shown in FIG. 3C and spaced apart according to an alternate embodiment of the present invention.

Referring to FIG. 20, showing a compression gauge cartridge 30 in a perspective view in an embodiment of the present invention, compression gauge cartridge 30 for use mounted in a cartridge bay of a cartridge jaw member comprising an end effector of a surgical stapler instrument to compress a tissue and measure a reactionary load therefrom for assisting in selection of a staple cartridge optimal for a tissue of a surgical stapling operation comprises: a cartridge body 31; and a force gauge assembly 40, an electronic circuit module 135 including a signal processing circuit for conditioning and digitizing a signal from said force gauge assembly 40 and wireless transmission circuit, and a battery module 136 for providing operational power to said force gauge assembly 40 and said electronic circuit module 135 housed in said cartridge body 31. In an embodiment, there is provided a corresponding force transducer indicator (not shown in the FIGURE) configured to receive and display a wireless signal from compression gauge cartridge 30 indicating the result of measurement by said force gauge assembly 40. In an embodiment said battery module 136 may be of rechargeable type.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While preferred illustrative embodiments of the invention are described above, it will be apparent to those skilled in the art that various changes and modifications may be made therein without departing from the invention. Accordingly, the appended claims should be used to interpret the scope of the present invention.

What is claimed is:

1. A surgical instrument for compressing a tissue to measure the reactionary load therefrom for assisting selection of staple cartridge and assessing the condition of the tissue comprising:
   a handle portion;
   a body portion extending distally from said handle portion and defining a longitudinal axis; and
   a tool assembly at the distal end of and operatively connected to said body portion, said tool assembly comprising a first jaw member having a tissue supporting surface and a second jaw member having a tissue contacting surface, configured to open and close when operated by said handle portion to capture and compress said tissue;
   wherein said first jaw member comprises a transducer means for producing an electrical signal indicative of force acting thereon and a compression head disposed to provide a mechanical interface between said transducer means and said tissue, compressed between said first and second jaw members, transmitting said reactionary load from said tissue to said transducer means.

2. The surgical instrument of claim 1, wherein said first jaw member further comprises a spacer member disposed between said tissue contacting surface of said second jaw member and said tissue supporting surface of said first jaw member and proximally with respect to said transducer means.

3. The surgical instrument of claim 2, wherein said spacer member is of a rigid construction extending from said tissue supporting surface of said first jaw member.

4. The surgical instrument of claim 1, wherein said surgical instrument further comprises a signal conduction wire and a transducer indicator for bi-directionally conducting an electrical signal from said transducer means to said transducer indicator disposed remotely from a surgical site for signal processing and display and a power and control signals from said transducer indicator needed for operation of said transducer means.

5. The surgical instrument of claim 1, wherein said transducer means comprises a force transducer based on a strain gauge of type selected from the group including a beam type and a button type.

6. The surgical instrument of claim 1, wherein said transducer means is of a planar configuration.

7. A cartridge for use mounted in a first jaw member comprising an end effector, together with a second jaw member having a tissue contacting surface, of a surgical instrument to measure reactionary force from a tissue captured and compressed between said first and second jaw member comprising:

a cartridge body having a tissue supporting surface, a transducer means for producing an electrical signal indicative of force acting thereon and a compression head supported in said cartridge body, said compression head configured to mechanically interface said transducer means and said tissue, compressed between said first and second jaw member, transmitting said reactionary force from said tissue to said transducer means.

8. The cartridge of claim 7, wherein said cartridge body further comprises a spacer member of a rigid construction extending from said tissue supporting surface and disposed proximally with respect to said transducer means.

9. The cartridge of claim 7, wherein said cartridge further comprises a signal conduction wire and a transducer indicator for bi-directionally conducting an electrical signal from said transducer means to said transducer indicator disposed remotely from a surgical site for signal processing and display and a power and control signals from said transducer indicator needed for operation of said transducer means.

10. The cartridge of claim 7, wherein said transducer means comprises a force transducer based on a strain gauge of type selected from the group including a beam type and a button type.

11. The of claim 7, wherein said transducer means is of a planar configuration.

* * * * *